US008722381B2

(12) United States Patent
Ramer et al.

(10) Patent No.: US 8,722,381 B2
(45) Date of Patent: May 13, 2014

(54) VARIANTS OF A BACILLUS STREAROTHERMOPHILUS ALPHA-AMYLASE AND USES THEREOF

(75) Inventors: Sandra W. Ramer, Sunnyvale, CA (US); Michael J. Pepsin, Castro Valley, CA (US); Andrew Shaw, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 637 days.

(21) Appl. No.: 12/365,411

(22) Filed: Feb. 4, 2009

(65) Prior Publication Data

US 2009/0226569 A1 Sep. 10, 2009

Related U.S. Application Data

(60) Provisional application No. 61/063,639, filed on Feb. 4, 2008.

(51) Int. Cl.
| | | |
|---|---|---|
| *C12N 9/28* | (2006.01) | |
| *C12P 19/14* | (2006.01) | |
| *C12P 19/04* | (2006.01) | |
| *C12P 7/06* | (2006.01) | |
| *C12P 7/08* | (2006.01) | |
| *C12P 7/14* | (2006.01) | |
| *C07H 21/04* | (2006.01) | |
| *A61K 9/68* | (2006.01) | |

(52) U.S. Cl.
USPC ............. 435/202; 435/99; 435/101; 435/161; 435/162; 435/163; 424/48; 536/23.2

(58) Field of Classification Search
None
See application file for complete search history.

(56) References Cited

U.S. PATENT DOCUMENTS

| | | | |
|---|---|---|---|
| 5,830,837 A | 11/1998 | Bisgård-Frantzen et al. | |
| 6,143,708 A | 11/2000 | Svendsen et al. | |
| 6,187,576 B1 | 2/2001 | Svendsen et al. | |
| 6,939,703 B2 | 9/2005 | Van Der Laan et al. | |
| 7,541,026 B2* | 6/2009 | Power et al. | 424/94.6 |
| 2002/0106725 A1* | 8/2002 | Stougaard et al. | 435/69.1 |
| 2007/0157329 A1* | 7/2007 | Callen et al. | 800/18 |

FOREIGN PATENT DOCUMENTS

WO WO 2009/061381 A2 5/2009

OTHER PUBLICATIONS

Whisstock et al. Quaterly Reviews of Biophysics, 2003, "Prediction of protein function from protein sequence and structure", 36(3): 307-340.*
Chica et al. Semi-rational approaches to engineering enzyme activity: combining the benefits of directed evolution and rational design, Curr Opin Biotechnol. Aug. 2005;16(4):378-84. Review.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Takkinen et al. Amino acid sequence of alpha-amylase from *Bacillus amyloliquefaciens* deduced from the nucleotide sequence of the cloned gene, JBC 258: 1007-1013, 1983.*
Fogarty et al., in Progress in Industrial Microbiology, 15:112-115 (1979).
Holm, Liisa et al., "Random mutagenesis used to probe the structure and function of *Bacillus stearothermophilus* alpha-amylase," *Protein Engineering*, 3(3):181-191 (1990).
Database Genseq [Online] Sep. 4, 2000, "*Bacillus amyloliquefaciens* Termamyl-like alpha-amylase." XP002535925 retrieved from EBI accession No. GSP:AAY99606, Database accession No. AAY99606 abstract.
Database Genseq [Online] Oct. 19, 2000, "*Bacillus amyloliquefaciens* clone number 25 protein, Seq ID No. 7." XP002535926 retrieved from EBI accession No. GSP:AAB12432, Database accession No. AAB12432 abstract.
Database Genseq [Online] Mar. 24, 2005, "Alpha-amylase for starch hydrolysis, Seq ID No. 9." XP002535928 retrieved from EBI accession No. GSP:ADW21539, Database accession No. ADW21539 abstract.
Database UniProt [Online] Feb. 1, 2005, "SubName: Full=Alpha-amylase; Flags: Fragment;" XP002535927 retrieved from EBI accession No. UNIPROT:Q5MB94, Database accession No. Q5MB94 abstract.
Sajedi, Reza Hassan et al., "Nucleotide Sequence, Structural Investigation and Homology Modeling Studies of a $Ca^{2+}$-independent α-amylase with Acidic pH-profile," *Journal of Biochemistry and Molecular Biology*, 40(3):315-324 (2007).

\* cited by examiner

*Primary Examiner* — Iqbal H Chowdhury
(74) *Attorney, Agent, or Firm* — Danisco US Inc.

(57) ABSTRACT

Described are variants of alpha (α)-amylases having altered starch hydrolysis profiles. The variants have improved thermostability and increased specific activity, resulting in reduced peak viscosity and altered final viscosity during starch liquefaction. The amylase variants are useful, e.g., in liquefaction and other starch degradation processes.

42 Claims, 13 Drawing Sheets

SEQ ID NO:1 WILD-TYPE
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
IGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

SEQ ID NO:2 VARIANT I181A
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
AGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

SEQ ID NO:3 VARIANT I181P
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
PGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

SEQ ID NO:4 VARIANT I181C
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
CGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

FIG. 8

SEQ ID NO:5 VARIANT I181D
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
DGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

SEQ ID NO:6 VARIANT I181E
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
EGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

SEQ ID NO:7 VARIANT I181F
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
FGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

SEQ ID NO:8 VARIANT I181G
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
GGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

FIG. 8 (cont.)

SEQ ID NO:9 VARIANT I181H
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
HGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

SEQ ID NO:10 VARIANT I181L
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
LGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

SEQ ID NO:11 VARIANT I181R
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
RGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

SEQ ID NO:12 VARIANT I181S
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
SGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

FIG. 8 (cont.)

SEQ ID NO:13 VARIANT I181T
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
TGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

SEQ ID NO:14 VARIANT I181V
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
VGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

SEQ ID NO:15 VARIANT I181Y
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
YGKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

SEQ ID NO:16 VARIANT G182A
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
IAKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

FIG. 8 (cont.)

SEQ ID NO:17 VARIANT G182S
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
ISKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

SEQ ID NO:18 VARIANT G182P
AAPFNGTMMQYFEWYLPDDGTLWTKVANEANNLSSLGITALWLPPAYKGTSRSDVGYGVY
DLYDLGEFNQKGTVRTKYGTKAQYLQAIQAAHAAGMQVYADVVFDHKGGADGTEWVDAVE
VNPSDRNQEISGTYQIQAWTKFDFPGRGNTYSSFKWRWYHFDGVDWDESRKLSRIYKFRG
IPKAWDWEVDTENGNYDYLMYADLDMDHPEVVTELKNWGKWYVNTTNIDGFRLDAVKHIK
FSFFPDWLSYVRSQTGKPLFTVGEYWSYDINKLHNYITKTNGTMSLFDAPLHNKFYTASK
SGGAFDMRTLMTNTLMKDQPTLAVTFVDNHDTEPGQALQSWVDPWFKPLAYAFILTRQEG
YPCVFYGDYYGIPQYNIPSLKSKIDPLLIARRDYAYGTQHDYLDHSDIIGWTREGVTEKP
GSGLAALITDGPGGSKWMYVGKQHAGKVFYDLTGNRSDTVTINSDGWGEFKVNGGSVSVW
VPRKTTVSTIARPITTRPWTGEFVRWTEPRLVAWP

FIG. 8 (cont.)

```
                              SEQUENCE LISTING

<160> NUMBER OF SEQ ID NOS: 18

<210> SEQ ID NO 1
<211> LENGTH: 515
<212> TYPE: PRT
<213> ORGANISM: Bacillus stearothermophilus

<400> SEQUENCE: 1

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255
```

```
Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 2
<211> LENGTH: 515
<212> TYPE: PRT
<213> ORGANISM: Artificial Sequence
<220> FEATURE:
<223> OTHER INFORMATION: Synthetic variant I181A derived from Bacillus
      stearothermophilus alpha-amylase

<400> SEQUENCE: 2

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95
```

```
Gln Val Tyr Ala Asp Val Val Phe Asp His Lys Gly Ala Asp Gly
            100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ala Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
                195                 200                 205

Pro Glu Val Val Thr Glu Leu Lys Asn Trp Gly Lys Trp Tyr Val Asn
            210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
        290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
                355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
        450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515
```

```
<210> SEQ ID NO 3
<211> LENGTH: 515
<212> TYPE: PRT
<213> ORGANISM: Artificial Sequence
<220> FEATURE:
<223> OTHER INFORMATION: Synthetic variant I181P derived from Bacillus
      stearothermophilus alpha-amylase

<400> SEQUENCE: 3
```

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Pro Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

```
Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 4
<211> LENGTH: 515
<212> TYPE: PRT
<213> ORGANISM: Artificial Sequence
<220> FEATURE:
<223> OTHER INFORMATION: Synthetic variant I181C derived from Bacillus
      stearothermophilus alpha-amylase

<400> SEQUENCE: 4

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Cys Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
            195                 200                 205
```

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
                275                 280                 285

Ala Pro Leu His Asn Lys Phe Tyr Thr Ala Ser Lys Ser Gly Gly Ala
            290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
                355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 5
<211> LENGTH: 515
<212> TYPE: PRT
<213> ORGANISM: Artificial Sequence
<220> FEATURE:
<223> OTHER INFORMATION: Synthetic variant I181D derived from Bacillus
      stearothermophilus alpha-amylase

<400> SEQUENCE: 5

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

| | | | | | | | | | | | |
|---|---|---|---|---|---|---|---|---|---|---|---|
|Gly|Thr|Ser|Arg|Ser|Asp|Val|Gly|Tyr|Gly|Val|Tyr|Asp|Leu|Tyr|Asp|
| |50| | | |55| | | |60| | | | | | |

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                    85                  90                  95

Gln Val Tyr Ala Asp Val Val Phe Asp His Lys Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
            130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Asp Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp

```
                465                 470                 475                 480
Val Pro Arg Lys Thr Thr Val Ser Thr Ile Ala Arg Pro Ile Thr Thr
                    485                 490                 495

Arg Pro Trp Thr Gly Glu Phe Val Arg Trp Thr Glu Pro Arg Leu Val
            500                 505                 510

Ala Trp Pro
        515

<210> SEQ ID NO 6
<211> LENGTH: 515
<212> TYPE: PRT
<213> ORGANISM: Artificial Sequence
<220> FEATURE:
<223> OTHER INFORMATION: Synthetic variant I181E derived from Bacillus
      stearothermophilus alpha-amylase

<400> SEQUENCE: 6

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Glu Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
```

-continued

```
            305                 310                 315                 320
Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
                355                 360                 365

Tyr Tyr Gly Ile Pro Gln Tyr Asn Ile Pro Ser Leu Lys Ser Lys Ile
                370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
                435                 440                 445

Phe Tyr Asp Leu Thr Gly Asn Arg Ser Asp Thr Val Thr Ile Asn Ser
                450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
      515

<210> SEQ ID NO 7
<211> LENGTH: 515
<212> TYPE: PRT
<213> ORGANISM: Artificial Sequence
<220> FEATURE:
<223> OTHER INFORMATION: Synthetic variant I181F derived from Bacillus
      stearothermophilus alpha-amylase

<400> SEQUENCE: 7

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
                35                  40                  45

Gly Thr Ser Arg Ser Asp Val Gly Tyr Gly Val Tyr Asp Leu Tyr Asp
                50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
                115                 120                 125

Glu Ile Ser Gly Thr Tyr Gln Ile Gln Ala Trp Thr Lys Phe Asp Phe
                130                 135                 140

Pro Gly Arg Gly Asn Thr Tyr Ser Ser Phe Lys Trp Arg Trp Tyr His
```

```
              145                 150                 155                 160
Phe Asp Gly Val Asp Trp Asp Glu Ser Arg Lys Leu Ser Arg Ile Tyr
                165                 170                 175
Lys Phe Arg Gly Phe Gly Lys Ala Trp Asp Trp Glu Val Asp Thr Glu
                180                 185                 190
Asn Gly Asn Tyr Asp Tyr Leu Met Tyr Ala Asp Leu Asp Met Asp His
                195                 200                 205
Pro Glu Val Val Thr Glu Leu Lys Asn Trp Gly Lys Trp Tyr Val Asn
            210                 215                 220
Thr Thr Asn Ile Asp Gly Phe Arg Leu Asp Ala Val Lys His Ile Lys
225                 230                 235                 240
Phe Ser Phe Phe Pro Asp Trp Leu Ser Tyr Val Arg Ser Gln Thr Gly
                245                 250                 255
Lys Pro Leu Phe Thr Val Gly Glu Tyr Trp Ser Tyr Asp Ile Asn Lys
                260                 265                 270
Leu His Asn Tyr Ile Thr Lys Thr Asn Gly Thr Met Ser Leu Phe Asp
            275                 280                 285
Ala Pro Leu His Asn Lys Phe Tyr Thr Ala Ser Lys Ser Gly Gly Ala
        290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                325                 330                 335
Ala Leu Gln Ser Trp Val Asp Pro Trp Phe Lys Pro Leu Ala Tyr Ala
            340                 345                 350
Phe Ile Leu Thr Arg Gln Glu Gly Tyr Pro Cys Val Phe Tyr Gly Asp
            355                 360                 365
Tyr Tyr Gly Ile Pro Gln Tyr Asn Ile Pro Ser Leu Lys Ser Lys Ile
        370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
                405                 410                 415
Thr Glu Lys Pro Gly Ser Gly Leu Ala Ala Leu Ile Thr Asp Gly Pro
            420                 425                 430
Gly Gly Ser Lys Trp Met Tyr Val Gly Lys Gln His Ala Gly Lys Val
        435                 440                 445
Phe Tyr Asp Leu Thr Gly Asn Arg Ser Asp Thr Val Thr Ile Asn Ser
    450                 455                 460
Asp Gly Trp Gly Glu Phe Lys Val Asn Gly Gly Ser Val Ser Val Trp
465                 470                 475                 480
Val Pro Arg Lys Thr Thr Val Ser Thr Ile Ala Arg Pro Ile Thr Thr
                485                 490                 495
Arg Pro Trp Thr Gly Glu Phe Val Arg Trp Thr Glu Pro Arg Leu Val
                500                 505                 510
Ala Trp Pro
        515

<210> SEQ ID NO 8
<211> LENGTH: 515
<212> TYPE: PRT
<213> ORGANISM: Artificial Sequence
<220> FEATURE:
<223> OTHER INFORMATION: Synthetic variant I181G derived from Bacillus
      stearothermophilus alpha-amylase
```

<400> SEQUENCE: 8

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Gly Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415
```

```
Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 9
<211> LENGTH: 515
<212> TYPE: PRT
<213> ORGANISM: Artificial Sequence
<220> FEATURE:
<223> OTHER INFORMATION: Synthetic variant I181H derived from Bacillus
      stearothermophilus alpha-amylase

<400> SEQUENCE: 9

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly His Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255
```

```
Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 10
<211> LENGTH: 515
<212> TYPE: PRT
<213> ORGANISM: Artificial Sequence
<220> FEATURE:
<223> OTHER INFORMATION: Synthetic variant I181L derived from Bacillus
      stearothermophilus alpha-amylase

<400> SEQUENCE: 10

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95
```

-continued

```
Gln Val Tyr Ala Asp Val Val Phe Asp His Lys Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Leu Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515
```

<210> SEQ ID NO 11
<211> LENGTH: 515
<212> TYPE: PRT
<213> ORGANISM: Artificial Sequence
<220> FEATURE:
<223> OTHER INFORMATION: Synthetic variant I181R derived from Bacillus stearothermophilus alpha-amylase

<400> SEQUENCE: 11

```
Ala Ala Pro Phe Asn Gly Thr Met Met Gln Tyr Phe Glu Trp Tyr Leu
 1               5                  10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Arg Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365
```

```
Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 12
<211> LENGTH: 515
<212> TYPE: PRT
<213> ORGANISM: Artificial Sequence
<220> FEATURE:
<223> OTHER INFORMATION: Synthetic variant I181S derived from Bacillus
      stearothermophilus alpha-amylase

<400> SEQUENCE: 12

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ser Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205
```

-continued

```
Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 13
<211> LENGTH: 515
<212> TYPE: PRT
<213> ORGANISM: Artificial Sequence
<220> FEATURE:
<223> OTHER INFORMATION: Synthetic variant I181T derived from Bacillus
      stearothermophilus alpha-amylase

<400> SEQUENCE: 13

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45
```

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Thr Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp

```
                        465                 470                 475                 480
                Val Pro Arg Lys Thr Thr Val Ser Thr Ile Ala Arg Pro Ile Thr Thr
                                    485                 490                 495

Arg Pro Trp Thr Gly Glu Phe Val Arg Trp Thr Glu Pro Arg Leu Val
                                500                 505                 510

Ala Trp Pro
                        515

<210> SEQ ID NO 14
<211> LENGTH: 515
<212> TYPE: PRT
<213> ORGANISM: Artificial Sequence
<220> FEATURE:
<223> OTHER INFORMATION: Synthetic variant I181V derived from Bacillus
      stearothermophilus alpha-amylase

<400> SEQUENCE: 14

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Val Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
```

```
                305                 310                 315                 320
Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
                355                 360                 365

Tyr Tyr Gly Ile Pro Gln Tyr Asn Ile Pro Ser Leu Lys Ser Lys Ile
            370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515

<210> SEQ ID NO 15
<211> LENGTH: 515
<212> TYPE: PRT
<213> ORGANISM: Artificial Sequence
<220> FEATURE:
<223> OTHER INFORMATION: Synthetic variant I181Y derived from Bacillus
      stearothermophilus alpha-amylase

<400> SEQUENCE: 15

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
```

```
                145                 150                 155                 160
Phe Asp Gly Val Asp Trp Asp Glu Ser Arg Lys Leu Ser Arg Ile Tyr
                    165                 170                 175
Lys Phe Arg Gly Tyr Gly Lys Ala Trp Asp Trp Glu Val Asp Thr Glu
                    180                 185                 190
Asn Gly Asn Tyr Asp Tyr Leu Met Tyr Ala Asp Leu Asp Met Asp His
                    195                 200                 205
Pro Glu Val Val Thr Glu Leu Lys Asn Trp Gly Lys Trp Tyr Val Asn
                    210                 215                 220
Thr Thr Asn Ile Asp Gly Phe Arg Leu Asp Ala Val Lys His Ile Lys
225                 230                 235                 240
Phe Ser Phe Phe Pro Asp Trp Leu Ser Tyr Val Arg Ser Gln Thr Gly
                    245                 250                 255
Lys Pro Leu Phe Thr Val Gly Glu Tyr Trp Ser Tyr Asp Ile Asn Lys
                    260                 265                 270
Leu His Asn Tyr Ile Thr Lys Thr Asn Gly Thr Met Ser Leu Phe Asp
                    275                 280                 285
Ala Pro Leu His Asn Lys Phe Tyr Thr Ala Ser Lys Ser Gly Gly Ala
                    290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                    325                 330                 335
Ala Leu Gln Ser Trp Val Asp Pro Trp Phe Lys Pro Leu Ala Tyr Ala
                    340                 345                 350
Phe Ile Leu Thr Arg Gln Glu Gly Tyr Pro Cys Val Phe Tyr Gly Asp
                    355                 360                 365
Tyr Tyr Gly Ile Pro Gln Tyr Asn Ile Pro Ser Leu Lys Ser Lys Ile
                    370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
                    405                 410                 415
Thr Glu Lys Pro Gly Ser Gly Leu Ala Ala Leu Ile Thr Asp Gly Pro
                    420                 425                 430
Gly Gly Ser Lys Trp Met Tyr Val Gly Lys Gln His Ala Gly Lys Val
                    435                 440                 445
Phe Tyr Asp Leu Thr Gly Asn Arg Ser Asp Thr Val Thr Ile Asn Ser
                    450                 455                 460
Asp Gly Trp Gly Glu Phe Lys Val Asn Gly Gly Ser Val Ser Val Trp
465                 470                 475                 480
Val Pro Arg Lys Thr Thr Val Ser Thr Ile Ala Arg Pro Ile Thr Thr
                    485                 490                 495
Arg Pro Trp Thr Gly Glu Phe Val Arg Trp Thr Glu Pro Arg Leu Val
                    500                 505                 510
Ala Trp Pro
        515

<210> SEQ ID NO 16
<211> LENGTH: 515
<212> TYPE: PRT
<213> ORGANISM: Artificial Sequence
<220> FEATURE:
<223> OTHER INFORMATION: Synthetic variant G182A derived from Bacillus
      stearothermophilus alpha-amylase
```

<400> SEQUENCE: 16

```
Ala Ala Pro Phe Asn Gly Thr Met Met Gln Tyr Phe Glu Trp Tyr Leu
1               5                   10                  15
Pro Asp Asp Gly Thr Leu Trp Thr Lys Val Ala Asn Glu Ala Asn Asn
            20                  25                  30
Leu Ser Ser Leu Gly Ile Thr Ala Leu Trp Leu Pro Pro Ala Tyr Lys
        35                  40                  45
Gly Thr Ser Arg Ser Asp Val Gly Tyr Gly Val Tyr Asp Leu Tyr Asp
    50                  55                  60
Leu Gly Glu Phe Asn Gln Lys Gly Thr Val Arg Thr Lys Tyr Gly Thr
65                  70                  75                  80
Lys Ala Gln Tyr Leu Gln Ala Ile Gln Ala Ala His Ala Ala Gly Met
                85                  90                  95
Gln Val Tyr Ala Asp Val Val Phe Asp His Lys Gly Gly Ala Asp Gly
            100                 105                 110
Thr Glu Trp Val Asp Ala Val Glu Val Asn Pro Ser Asp Arg Asn Gln
        115                 120                 125
Glu Ile Ser Gly Thr Tyr Gln Ile Gln Ala Trp Thr Lys Phe Asp Phe
    130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                165                 170                 175
Lys Phe Arg Gly Ile Ala Lys Ala Trp Asp Trp Glu Val Asp Thr Glu
            180                 185                 190
Asn Gly Asn Tyr Asp Tyr Leu Met Tyr Ala Asp Leu Asp Met Asp His
        195                 200                 205
Pro Glu Val Val Thr Glu Leu Lys Asn Trp Gly Lys Trp Tyr Val Asn
    210                 215                 220
Thr Thr Asn Ile Asp Gly Phe Arg Leu Asp Ala Val Lys His Ile Lys
225                 230                 235                 240
Phe Ser Phe Phe Pro Asp Trp Leu Ser Tyr Val Arg Ser Gln Thr Gly
                245                 250                 255
Lys Pro Leu Phe Thr Val Gly Glu Tyr Trp Ser Tyr Asp Ile Asn Lys
            260                 265                 270
Leu His Asn Tyr Ile Thr Lys Thr Asn Gly Thr Met Ser Leu Phe Asp
        275                 280                 285
Ala Pro Leu His Asn Lys Phe Tyr Thr Ala Ser Lys Ser Gly Gly Ala
    290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                325                 330                 335
Ala Leu Gln Ser Trp Val Asp Pro Trp Phe Lys Pro Leu Ala Tyr Ala
            340                 345                 350
Phe Ile Leu Thr Arg Gln Glu Gly Tyr Pro Cys Val Phe Tyr Gly Asp
        355                 360                 365
Tyr Tyr Gly Ile Pro Gln Tyr Asn Ile Pro Ser Leu Lys Ser Lys Ile
    370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
                405                 410                 415
```

```
Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515

<210> SEQ ID NO 17
<211> LENGTH: 515
<212> TYPE: PRT
<213> ORGANISM: Artificial Sequence
<220> FEATURE:
<223> OTHER INFORMATION: Synthetic variant G182S derived from Bacillus
      stearothermophilus alpha-amylase

<400> SEQUENCE: 17

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Ser Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240
```

```
Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 18
<211> LENGTH: 515
<212> TYPE: PRT
<213> ORGANISM: Artificial Sequence
<220> FEATURE:
<223> OTHER INFORMATION: Synthetic variant G182P derived from Bacillus
      stearothermophilus alpha-amylase

<400> SEQUENCE: 18

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
    50                  55                  60
```

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala His Ala Ala Gly Met
            85                  90                  95

Gln Val Tyr Ala Asp Val Val Phe Asp His Lys Gly Ala Asp Gly
            100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
            165                 170                 175

Lys Phe Arg Gly Ile Pro Lys Ala Trp Asp Trp Glu Val Asp Thr Glu
            180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
            245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
            290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
            325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
            370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
            405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
            450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr

-continued

```
                485                     490                     495
Arg Pro Trp Thr Gly Glu Phe Val Arg Trp Thr Glu Pro Arg Leu Val
            500                     505                     510

Ala Trp Pro
        515
```

VARIANTS OF A BACILLUS STREAROTHERMOPHILUS ALPHA-AMYLASE AND USES THEREOF

PRIORITY

The present application claims priority to U.S. Provisional Application Ser. No. 61/063,639, filed on Feb. 4, 2008, which is hereby incorporated by reference in its entirety.

TECHNICAL FIELD

Described are variants of α-amylase enzymes for use in industrial processes, such as liquefaction of starch. The α-amylase variants have increased specific activity allowing the more rapidly reduction of peak viscosity during liquefaction processes.

BACKGROUND

For many industrial processes that use starches as starting materials, it is desirable to have amylolytic enzymes that can function under high temperature to rapidly breakdown starch to release smaller carbohydrates, resulting in a reduction in viscosity. The more the viscosity drops, the more access such enzyme have to further cleave the starch, and the less mechanical power is required for mixing the reaction. A number of enzymes are useful for starch liquefaction, including the α-amylases from *Bacillus lichenformis* or *Geobacillus stearothermophilus*, AmyL and AmyS respectively, which are well-suited for liquefaction of starches at high temperature.

Generally, enzymes must be added to a liquefaction process in sufficient amounts to provide accomplish the objective, i.e., there must be sufficient enzyme activity (or catalytic activity) to liquefy the starch substrate within a preselected time-frame. Enzyme activity can be measured per unit of enzyme, and is called specific activity. Thus, an enzyme with lower specific activity must be used in greater amounts to provide a desired amount of enzyme activity in a given process. It is often advantageous to be able to make high specific activity enzyme preparations, allowing the use of a smaller amount to produce a desired effect. This can be accomplished, for example, by purifying a crude enzyme preparation. However, even a pure enzyme has a maximum specific activity for a given substrate under particular assay conditions.

The need exists for improved α-amylases that are suited for liquefaction of starches at high temperature.

SUMMARY

Provided herein are α-amylase variants for use in industrial processes of starch degradation. The variants amylase are based on the polypeptide sequence of a wild-type α-amylase from the organism *Bacillus stearothermophilus*, in particular the AmyS α-amylase.

The variant amylases are useful in that they have improved specific activity relative to the parent amylase from which they are derived, thereby providing improving performance in starch hydrolysis applications. The variant amylases are particularly useful in starch degradation processes, such as liquefaction for ethanol production processes and desizing of textiles and other woven materials. The enzymes are relatively thermostable, and have good activity under the conditions generally used for starch degradation. A feature of the variants amylases is that they posses improved properties in terms of reducing the initial viscosity of a starch slurry during liquefaction at high temperatures. Moreover, because the variant amylases can be used in lower amounts, both separately and in blends with other enzymes, they additional provide an economic benefit for both the end-user and the manufacturer.

Embodiments of the present compositions and methods include isolated variant α-amylases, compositions comprising these enzymes, and methods of using the enzymes or compositions, as well nucleic acids encoding the variant enzymes, expression vectors, and host cells that express the α-amylase variants.

In one aspect, a variant α-amylase derived from *Bacillus stearothermophilus* α-amylase is provided. The variant is altered at position 181 and/or 182 of the mature protein. Specifically, the wild-type sequence is altered such that the amino acids naturally-occurring at positions 181, 182, or both, are substituted with a different amino acid residue that is not present in the wild-type at that position. Preferably, the wild-type amino acid residue at position 181 is replaced with Ala, Cys, Asp, Glu, Leu, or Pro, and/or the wild-type amino acid residue at position 182 is replaced with Ala, Ser, or Pro.

In another aspect, a composition is provided that comprises one or more variant α-amylases having α-amylase activity. The composition may further comprise one or more additional enzymes, such an enzyme having an activity that is useful for liquefaction of complex carbohydrates including amylose and amylopectins, e.g., a starch. In one example, a food-grade lyophilized composition comprising one or more of the variant α-amylases described or exemplified herein, is provided.

Also provided is a polynucleotide that encodes a variant α-amylase, such as those having an amino acid sequence of SEQ ID NOs: 1-17. Particular polynucleotides encode a polypeptide with the amino acid sequence of SEQ ID NOs: 2, 3, 4, 5, 10, 15, 17, or 19. Vectors comprising the polynucleotide, bacterial cells and host cells comprising one of the polynucleotides or vectors, and expression systems for expressing the encoded proteins, are also provided.

Methods of making and using the amylase variants and the compositions are also provided. In one aspect, a method of producing a composition comprising at least one variant of a wild-type α-amylase from *Bacillus stearothermophilus* is provided. The method comprises utilizing a host cell for a fermentation process wherein the at least one variant α-amylase is expressed. As above, the variant comprises a substitution at position 181 or 182 of the mature protein. The host cell is preferably a *Bacillus* sp., e.g., *B. lichenformis, B. subtilis*, or *B. stearothermophilus*. The method entails the final step of at least partially purifying the at least one variant α-amylase, thereby resulting in the production of composition comprising at least one variant α-amylase.

A method is provided for liquefying a starch slurry using an amylase variant as provided herein. The method comprises making a slurry comprising the starch, heating the slurry to an temperature acceptable for liquefaction, adding to the slurry a composition comprising at least one variant as described herein, and incubating the slurry with the composition for a time and at a temperature sufficient to liquefy the starch slurry.

Further provided is a method of treating a woven material that has been previously subjected to contact with a coating comprising starch or a starch-derivative. The method comprises contacting the woven material with a liquid comprising an α-amylase variant as provided hereinabove, for a time and under conditions sufficient to substantially remove the coating from the woven material.

Enzyme blends are also provided herein. The enzyme blends comprise at least a first and a second α-amylase. The first α-amylase has a catalytic activity that, when used in a liquefaction process, results in a final viscosity lower than that provided by the second α-amylase. The activity of the first α-amylase results in a peak viscosity that is higher than that which results from the activity of the second α-amylase, when each is used alone in comparable liquefaction processes. The enzyme blend provides an overall or combined catalytic activity that, when used in a liquefaction process, results in a final viscosity about the same as that resulting from the use of the first α-amylase alone in a comparable liquefaction process, and a peak viscosity substantially less than that resulting from the use of the second α-amylase alone in a comparable liquefaction process.

A method of liquefying a starch slurry using the enzyme blend is also provided. The method comprises making a slurry comprising the starch, heating the slurry to an acceptable temperature for liquefaction, adding an enzyme blend as provided above (e.g., comprising the first and second α-amylases) to the slurry, and incubating the slurry with the enzyme blend for a time and at a temperature sufficient to liquefy the starch slurry. Preferably, the method provides a final viscosity about as low as that resultant from the use of the first α-amylase alone in a comparable liquefaction process, and a peak viscosity lower than that resultant from the use of the second α-amylase alone in a comparable liquefaction process.

Methods of producing ethanol using the amylase variants, the compositions, and/or the enzyme blends disclosed herein, are also provided.

Methods of making the variant amylase enzymes, and methods of using the α-amylase variants and compositions and blends comprising the variants for liquefaction, and treating woven material to remove coatings are provided.

Also provided are kits for facilitating liquefaction of starch slurry. The kits comprise at least one of:

a variant α-amylase as provided hereinabove, a composition comprising an amylase variant as provided hereinabove, a food-grade lyophilized composition as provided hereinabove, or an enzyme blend as provided hereinabove; and instructions for use of the kit in the liquefaction of a starch slurry.

Particular aspects and embodiment of the present compositions and methods are set forth below:

In one aspect, a variant α-amylase based on a parental α-amylase from *Bacillus stearothermophilus* is provided, wherein the variant comprises a substitution at amino acid position 181 or 182, or both, compared to the parental α-amylase, wherein the amino acid residue at position 181 of the variant is selected from Pro, Ala, Leu, Cys, Asp, and Glu, and the amino acid residue at position 182 of the variant is selected from Pro, Ala, and Ser.

In some embodiments, the variant α-amylase has an amino acid sequence selected from the group consisting of SEQ ID NO: 3 (I181P), SEQ ID NO: 2 (I181A), SEQ ID NO: 10 (I181L), SEQ ID NO: 4 (I181C), SEQ ID NO: 5 (I181D), SEQ ID NO: 6 (I181E), and SEQ ID NO: 15 (I181Y). In some embodiments, the variant α-amylase has an amino acid sequence selected from the group consisting of SEQ ID NO: 18 (G182P), SEQ ID NO: 16 (G182A), and SEQ ID NO: 17 (G182S).

In some embodiments, the parental α-amylase has an amino acid sequence at least 85% identical to the amino acid sequence of SEQ ID NO: 1. In particular embodiments, the parental α-amylase has the amino acid sequence of SEQ ID NO: 1.

In some embodiments, the variant α-amylase has increased specific activity compared to the wild-type α-amylase, under specified assay conditions. In some embodiments, the variant has increased specific activity between about 50-90° C. In particular embodiments, the variant α-amylase has increased specific activity between about 65-85° C.

In another aspect, a composition comprising a variant α-amylase is provided. In some embodiments, the composition comprises at least one additional enzyme. In some embodiments, the at least one additional enzyme has activity useful for liquefaction of a complex carbohydrate comprising amylose and amylopectins. In particular embodiments, the at least one additional enzymes is an additional α-amylase.

In some embodiments, the composition in a liquefaction process reduces the peak viscosity of a starch slurry relative to that of a comparable starch slurry liquefied with the additional enzyme in the absence of the variant α-amylase.

In some embodiments, the composition is formulated for use in food or food processes. A related embodiment is a food-grade lyophilized composition comprising a variant α-amylase.

In another aspect, a polynucleotide that encodes a variant α-amylase is provided. In some embodiments, the codon usage of the polynucleotide is optimized for expression of the variant α-amylase in a microorganism or a plant.

In some embodiments, an expression vector comprising a polynucleotide that encodes a variant α-amylase is provided. In a related embodiment, a bacterial cell comprising the expression vector is provided. In another related embodiment, a host cell comprising a polynucleotide that encodes a variant α-amylase is provided. The polynucleotide may be in an expression vector. The host cell may be *Bacillus licheniformis, Bacillus subtilis*, or *Bacillus stearothermophilus*. The host cell may alternatively be a plant and the plant may be used for ethanol production.

In another aspect, a method of liquefying a starch slurry is provided, comprising:

making a slurry comprising the starch;

heating the slurry to a temperature acceptable for starch liquefaction;

adding to the slurry a composition of claim 7; and incubating the slurry with the composition for a time and at a temperature sufficient to liquefy the starch slurry.

In some embodiments of the method, the temperature is from about 50° C. to about 95° C. In some embodiments of the method, the slurry comprises about 15-40% starch on a dry-weight basis.

In some embodiments of the method, the liquefaction is part of a fermentation process. In some embodiments of the method, the fermentation is used to produce a food product, a food additive, a fuel, or a fuel additive. In some embodiments of the method, the fuel or fuel additive is an alcohol. In particular embodiments, the alcohol is ethanol.

In some embodiments of the method, the incubating step results in a peak viscosity that is reduced by at least 25% relative to the peak viscosity of a comparable slurry liquefied by the parental α-amylase.

In another aspect, a method of treating a woven material that has previously been subjected to contact with a coating comprising starch or a starch-derivative is provided, the method comprising contacting the woven material with a solution comprising a variant α-amylase for a time and under conditions sufficient to substantially remove the coating from the woven material. In some embodiments, the woven material is a fabric. In some embodiments, the contacting step is performed at a pressure that is greater then ambient atmospheric pressure.

In another aspect, an enzyme blend for liquefying a starch slurry is provided, the blend comprising:

at least a first and a second α-amylase, the first α-amylase having a catalytic activity that, when used in a liquefaction process, results in a final viscosity lower than, but a peak viscosity higher than, a corresponding catalytic activity of the second α-amylase, when each amylase is used alone in comparable liquefaction processes, wherein when used in comparable liquefaction processes, the enzyme blend provides catalytic activity that results in a final viscosity about the same as that resulting from the use of the first α-amylase alone, and a peak viscosity substantially less than that resulting from the use of the second α-amylase alone;

wherein comparable liquefaction processes comprise specified conditions of temperature, pH, calcium ion concentration, and substrate concentration.

In a related aspect, a method of liquefying a starch slurry is provided comprising making a slurry comprising the starch, heating the slurry to an acceptable temperature for liquefaction, adding an enzyme blend comprising said first and second α-amylases to the slurry, and incubating the slurry with the enzyme blend for a time and at a temperature sufficient to liquefy the starch slurry. In some embodiments, the final viscosity is about as low as that resultant from the use of the first α-amylase alone in a comparable liquefaction process, and the peak viscosity is lower than that resultant from the use of the second α-amylase alone in a comparable liquefaction process. In some embodiments, the amount of enzyme blend added results in the addition of less of each of the first and second α-amylases than the corresponding amounts of the first and second α-amylases, respectively, added when each is used alone in a comparable liquefaction process. In some embodiments, the amount of each of the first and second α-amylases, respectively, is about half the corresponding amount added when each is used alone.

In another aspect, a method of producing ethanol is provided, comprising:

liquefying a starch slurry with one or more of:

(a) a variant α-amylase based on a parental α-amylase from *Bacillus stearothermophilus*, wherein the variant comprises a substitution at amino acid position 181 or 182, or both, compared to the parental α-amylase, wherein the amino acid residue at position 181 of the variant is selected from Pro, Ala, Leu, Cys, Asp, and Glu, and the amino acid residue at position 182 of the variant is selected from Pro, Ala, and Ser, (b) a composition comprising the variant α-amylase of (a), (c) a food-grade lyophilized composition comprising the variant α-amylase of (a), or (d) an enzyme blend comprising the variant α-amylase of (a) and a second amylase, the variant α-amylase having a catalytic activity that, when used in a liquefaction process, results in a final viscosity lower than, but a peak viscosity higher than, a corresponding catalytic activity of the second α-amylase, when each of the variant α-amylase and second amylase is used alone in comparable liquefaction processes;

fermenting at least a portion of the sugars in the slurry to produce ethanol; and at least partially purifying the resultant ethanol.

In some embodiments, the optional step of adding one or more additional enzymes to the liquefied starch slurry to further effectuate the production of ethanol during the fermenting step.

In yet another aspect, a kit for facilitating liquefaction of starch slurry is provided, the kit comprising:

at least one of:

(a) a variant α-amylase based on a parental α-amylase from *Bacillus stearothermophilus*, wherein the variant comprises a substitution at amino acid position 181 or 182, or both, compared to the parental α-amylase, wherein the amino acid residue at position 181 of the variant is selected from Pro, Ala, Leu, Cys, Asp, and Glu, and the amino acid residue at position 182 of the variant is selected from Pro, Ala, and Ser, (b) a composition comprising the variant α-amylase of (a), (c) a food-grade lyophilized composition comprising the variant α-amylase of (a), or (d) an enzyme blend comprising the variant α-amylase of (a) and a second amylase, the variant α-amylase having a catalytic activity that, when used in a liquefaction process, results in a final viscosity lower than, but a peak viscosity higher than, a corresponding catalytic activity of the second α-amylase, when each of the variant α-amylase and second amylase is used alone in comparable liquefaction processes; and instructions for use of the kit in the liquefaction of a starch slurry.

These and other aspects of the present compositions and method will be apparent in view of the following description and drawings.

BRIEF DESCRIPTION OF THE DRAWINGS

FIG. 8 shows a list of the sequences used in the application.

BRIEF DESCRIPTION OF THE SEQUENCES

Figure 1:
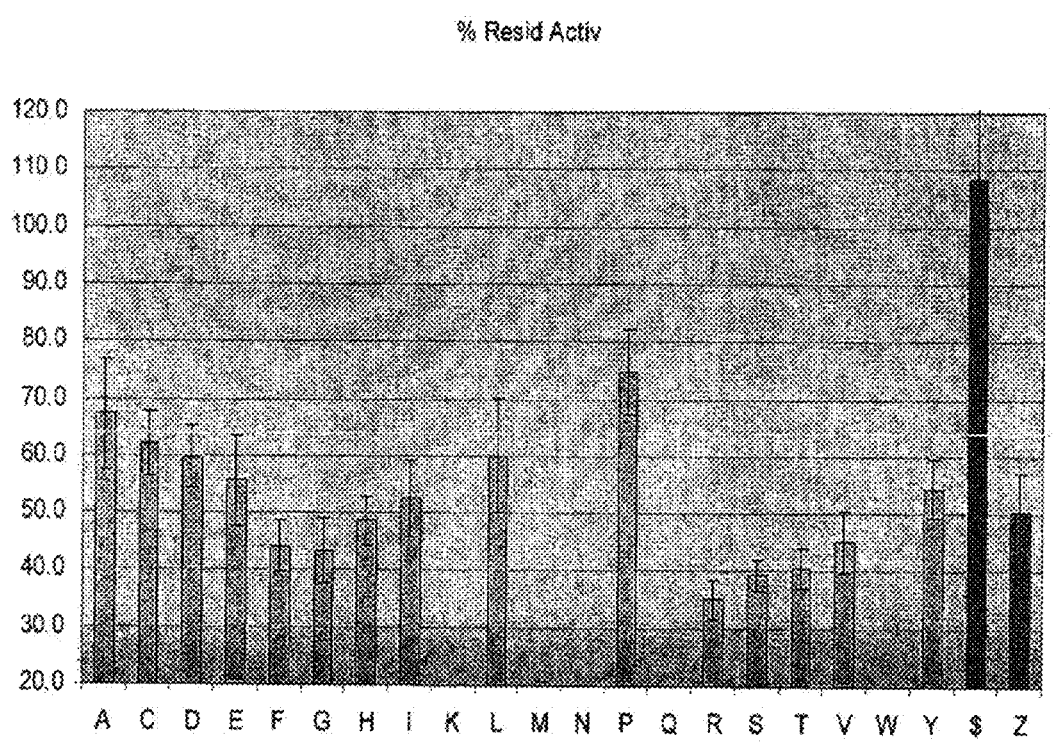
FIG. 1 shows the results of a thermostability screen on variants of the AmyS α-amylase at position 181.

SEQ ID NO: 1 is the amino acid sequence of the parental/wild-type *Bacillus stearothermophilus* α-amylase.

SEQ ID NO: 2 is the amino acid sequence of a variant α-amylase based on the parental/wild-type *Bacillus stearothermophilus* α-amylase, the variant having the substitution I181A.

SEQ ID NO: 3 is the amino acid sequence of a variant α-amylase based on the parental/wild-type *Bacillus stearothermophilus* α-amylase, the variant having the substitution I181P.

SEQ ID NO: 4 is the amino acid sequence of a variant α-amylase based on the parental/wild-type *Bacillus stearothermophilus* α-amylase, the variant having the substitution I181C.

SEQ ID NO: 5 is the amino acid sequence of a variant α-amylase based on the parental/wild-type *Bacillus stearothermophilus* α-amylase, the variant having the substitution I181D.

SEQ ID NO: 6 is the amino acid sequence of a variant α-amylase based on the parental/wild-type *Bacillus stearothermophilus* α-amylase, the variant having the substitution I181E.

SEQ ID NO: 7 is the amino acid sequence of a variant α-amylase based on the parental/wild-type *Bacillus stearothermophilus* α-amylase, the variant having the substitution I181F.

SEQ ID NO: 8 is the amino acid sequence of a variant α-amylase based on the parental/wild-type *Bacillus stearothermophilus* α-amylase, the variant having the substitution I181G.

SEQ ID NO: 9 is the amino acid sequence of a variant α-amylase based on the parental/wild-type *Bacillus stearothermophilus* α-amylase, the variant having the substitution I181H.

SEQ ID NO: 10 is the amino acid sequence of a variant α-amylase based on the parental/wild-type *Bacillus stearothermophilus* α-amylase, the variant having the substitution I181L.

SEQ ID NO: 11 is the amino acid sequence of a variant α-amylase based on the parental/wild-type *Bacillus stearothermophilus* α-amylase, the variant having the substitution I181R.

SEQ ID NO: 12 is the amino acid sequence of a variant α-amylase based on the parental/wild-type *Bacillus stearothermophilus* α-amylase, the variant having the substitution I181S.

SEQ ID NO: 13 is the amino acid sequence of a variant α-amylase based on the parental/wild-type *Bacillus stearothermophilus* α-amylase, the variant having the substitution I181T.

SEQ ID NO: 14 is the amino acid sequence of a variant α-amylase based on the parental/wild-type *Bacillus stearothermophilus* α-amylase, the variant having the substitution I181V.

SEQ ID NO: 15 is the amino acid sequence of a variant α-amylase based on the parental/wild-type *Bacillus stearothermophilus* α-amylase, the variant having the substitution I181Y.

SEQ ID NO: 16 is the amino acid sequence of a variant α-amylase based on the parental/wild-type *Bacillus stearothermophilus* α-amylase, the variant having the substitution G182A.

SEQ ID NO: 17 is the amino acid sequence of a variant α-amylase based on the parental/wild-type *Bacillus stearothermophilus* α-amylase, the variant having the substitution G182S.

SEQ ID NO: 18 is the amino acid sequence of a variant α-amylase based on the parental/wild-type *Bacillus stearothermophilus* α-amylase, the variant having the substitution G182P.

DETAILED DESCRIPTION

Alpha-amylase (α-amylase) variants that provide certain benefits and advantages over currently available α-amylases are described. The variant α-amylases exhibit relatively good thermostability and broad temperature optima, allowing them to be used in high-temperature starch liquefaction, for example for production of fermentation products such as alcohol, and especially ethanol. In addition, the variant α-amylases have improved specific activity (i.e., activity per unit of enzyme); therefore, less of the variant amylase can be used to accomplish the same result produced by the parental/wild-type amylase.

The amylase variants are useful for liquefaction processes and other starch degradation processes, such as desizing woven materials. The variant amylases can also be used in conjunction with each other, and or in conjunction with one or more other enzymes, for example in a blend. Preferably, the other enzymes are active under the same or similar reaction conditions as those used for the variant α-amylases. The use of an enzyme blend provides more flexibility to the end user, as well as certain economic and processing advantages to the end user and the manufacturer.

The discovery of variant enzymes that provide increased specific activity and altered performance in applications such as liquefaction provides manufacturers and end users with options for the production and use of amylases. Processing conditions, such as pH, temperature, ionic strength, and the presence of cofactors, can be selected to support the activity of the variant α-amylases and one or more other enzymes present in a blend. Such processing conditions can facilitate the use of continuous or semi-continuous processes, rather than costly and time-consuming batch processes.

A. DEFINITIONS AND ABBREVIATIONS

In accordance with this detailed description, the following abbreviations and definitions apply. The singular forms "a," "an," and "the" include plural referents unless the context clearly dictates otherwise. Thus, for example, reference to "an enzyme" includes a plurality of such enzymes, and reference to "the formulation" includes reference to one or more formulations and equivalents thereof known to those skilled in the art, and so forth.

The term "about" with respect to a numerical value or range indicates that the numerical value can be 10% greater or less than the stated value. In other embodiments, "about" indicates that a numerical value can be 5% greater or less than the stated value.

Unless defined otherwise, all technical and scientific terms used herein have the same meaning as commonly understood by one of ordinary skill in the art. The following terms are defined for clarity:

1. Definitions

"Amylase" means an enzyme that is, among other things, capable of catalyzing the degradation of starch, amylose, amylopectin, and the like. Generally, α-amylases (EC 3.2.1.1; α-D-(1→4)-glucan glucanohydrolase) are defined as endo-acting enzymes cleaving α-D-(1→4) O-glycosidic linkages in a polysaccharide containing three or more α-D-(1→4) linked glucose units. The α-amylases release reducing groups in the α-configuration. They act on starch, glycogen and related poly- and oligosaccharides in a random manner. In contrast, the exo-acting amylolytic enzymes sequentially cleave the substrate molecule from the non-reducing end. The glucan 1,4-α-maltohydrolases (maltogenic α-amylases; EC 3.2.1.133) produce α-maltose as the end product, while β-amylases (EC 3.2.1.2) produce β-maltose. β-Amylases, α-glucosidases (EC 3.2.1.20; α-D-glucoside glucohydrolase), glucoamylase (EC 3.2.1.3; α-D-(1→4)-glucan glucohydrolase), and product-specific amylases can produce malto-oligosaccharides of a specific length from their respective substrates. Glucoamylases release glucosyl residues from the non-reducing ends of amylose and amylopectin molecules. Glucoamylases also catalyze the hydrolysis of α-1,6 and α-1,3 linkages, although at much slower rate than α-1,4 linkages.

"α-Amylase variant," "α-amylase variant polypeptide," and "variant amylase" or "variant enzyme" mean an α-amylase protein that has an amino acid sequence that has been modified from the amino acid sequence of a wild-type α-amylase. As used herein, "parent enzymes," "parent sequence," "parent polypeptide," "wild-type α-amylase protein," and "parent polypeptides" mean enzymes and polypeptides from which the α-amylase variant polypeptides are based, e.g., a Bacillus or Geobacillus spp. α-amylase. Preferred herein as wild-type or parent enzymes are those from Bacillus stearothermophilus. A nucleic acid sequence encoding a parent polypeptide may be referred to herein as a "parent nucleic acid." A wild-type α-amylase occurs naturally. "α-amylase variants" differ from a wild-type α-amylase in the amino acid residues of the mature protein, i.e., the active molecule without a signal sequence, or other sequence that is removed post-transitionally, whether natural or artificial. An α-amylase variant can be "chimeric" or can be a "chimeric molecule", e.g., a fusion protein containing sequences from more than one polypeptide. For example, the α-amylase protein can comprise a mature α-amylase protein linked to the signal peptide of another α-amylase. An α-amylase variant can also be a chimeric in the sense that it contains a portion, region, or domain from one molecule fused to one or more portions, regions, or domains from one or more other molecules provided that the catalytic activity of an α-amylase is present in the resultant molecule. Chimeric molecules, as used herein are not naturally occurring. Preferred herein are enzyme variants wherein either one or two amino acid residues (positions 181 or 182, or both) are substituted with an amino acid residue that does not occur naturally in the referenced position.

"Activity" with respect to enzymes means catalytic activity and encompasses any acceptable measure of enzyme activity, such as the rate of activity, the amount of activity, or the specific activity. "Specific activity" is a measure of activity of an enzyme per unit of enzyme. Thus, specific activity may be expressed by unit weight or unit volume of enzyme. Further, specific activity may include a measure of purity of the enzyme. Specific activity in other cases will itself provide an indication of purity, for example, where a standard of activity is known, or available for comparison.

"Variants" as used herein refer to polypeptides or nucleic acids. The term "variant" may sometimes be used synonymously with the term "mutant." Variant polypeptides or nucleic acids include insertions, substitutions, deletions, transversions, truncations, and/or inversions at one or more locations in an amino acid or nucleotide sequence, relative to the parent polypeptide or nucleic acid. Variant nucleic acids can include sequences that are complementary to sequences that are capable of hybridizing to the nucleotide sequences presented herein. For example, a variant sequence is complementary to sequences capable of hybridizing under stringent conditions, e.g., 50° C. and 0.2×SSC (1×SSC=0.15 M NaCl, 0.015 M sodium citrate, pH 7.0), to the nucleotide sequences presented herein. More particularly, the term variant encompasses sequences that are complementary to sequences that are capable of hybridizing under highly stringent conditions, e.g., 65° C. and 0.1×SSC, to the nucleotide sequences presented herein. In various embodiments, a variant is at least 60, 65, 70, 75, 80, 85, 90, 91, 92, 93, 94, 95, 96, 97, 98, or even 99% identical to a sequence expressly provided herein.

As used herein, the term "expression" refers to the process by which a polypeptide is produced based on the nucleic acid sequence of a gene or artificial sequence. The process includes both transcription and translation. "Expression product" refers generally to a protein made by translation, whether in vivo or in vitro. Similarly, if a gene is expressed, the gene product (usually protein, but sometimes RNA) is produced in a cell, such as a host cell comprising the gene.

"Microorganism" as used herein, includes any bacterium, yeast, or fungus species.

"Isolated" with respect to protein, or nucleic acid sequences means that the sequence is at least substantially free from at least one other component that the sequence is naturally associated and found in nature. In the example of nucleic acid sequence, by isolated is meant isolated from genomic sequences.

"Purified" means that the material is in a relatively pure state, e.g., at least about 90% pure, at least about 95% pure, or at least about 98% pure. "Partially purified" encompasses lesser degrees of purity, provided that the protein or nucleic acid is "isolated" as the term is used herein.

"Thermostable" means the enzyme retains measurable activity after exposure to elevated temperatures. One measure of the thermostability of an enzyme, such as an α-amylase, is measured by its half-life ($t_{1/2}$), where half of the enzyme activity is lost by the half-life. The half-life value is calculated under defined conditions by measuring the residual amylase activity. In some embodiments, other measures of thermostability may be more useful or more practical, and may be measured and expressed, for example, as percent activity remaining after a specified exposure time and temperature of interest. Generally, after exposure of an enzyme to a temperature of interest for a desired time, the enzyme will be assayed under standard assay conditions, including temperature. Thermostable enzymes may also be thermoactive enzymes, i.e., they can exhibit activity when assayed at high temperatures. As used herein, thermostable enzymes can be both resistant to heat denaturation and active at high temperatures.

"pH range" means the ability of the enzyme to exhibit catalytic activity from acidic to basic conditions. Common processes in which α-amylases are used may include pH conditions spanning 5 or more pH units. As used herein, "pH stable" relates to the ability of the enzyme to retain measurable activity over a wide range of pHs, for example, 1, 2, 3, 4, 5, or even more pH units. In addition to pH stability, the variant α-amylases described herein may also provide a pH optimum, wherein activity is maximal at a certain pH or pH range, under conditions of temperature, time, substrate concentration, and calcium ion concentration that are otherwise held constant.

As used herein, "amino acid sequence" is sometimes used herein synonymously with the term "polypeptide" and/or the term "protein." In some instances, the term "amino acid sequence" is synonymous with the term "peptide"; in some instances, the term "amino acid sequence" is synonymous with the term "enzyme." In other cases, which will be clear from the context, the "amino acid sequence" will refer to the actual sequence ("primary sequence") of amino acid side chains or "residues" in the backbone of a polypeptide. For example, the Sequence Listing provided herewith provides the amino acid sequences for several polypeptides or domains of polypeptides.

As used herein, "nucleotide sequence" or "nucleic acid sequence" refers to an oligonucleotide sequence or polynucleotide sequence ("polynucleotide") and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA. As with polypeptides, the term "nucleotide sequence" is also used at times in discussion of the actual sequence of nucleotides or bases along a polynucleotide backbone, i.e., the primary sequence.

"Homologue" means an entity having a certain degree of identity or "homology" with the subject amino acid sequences and the subject nucleotide sequences. Typically, homologues will comprise the same active site residues as the subject amino acid sequence. Homologues also retain α-amylase activity, although the homologue may have different enzymatic properties than the subject protein. A "homologous sequence" includes a polynucleotide or a polypeptide having a certain percent identity, e.g., 80%, 85%, 86%, 87%, 88%, 89%, 90%, 91%, 92%, 93%, 94%, 95%, 96%, 97%, 98%, or 99%, with another sequence.

"Percent identity" means that a given percentage of bases or amino acid residues in a subject sequence or protein are the exactly the same base or residue as present in a reference sequence or protein, for example when comparing the two polypeptide sequences in an alignment. Amino acid sequences may be similar, but are not "identical" where an amino acid is substituted, deleted, or inserted in the subject sequence relative to the reference sequence. For proteins, the percent sequence identity is preferably measured between sequences that are in a similar state with respect to posttranslational modification. Typically, the "mature sequence" of the subject protein, i.e., that sequence which remains after processing to remove a signal sequence, is compared to a mature sequence of the reference protein. In other instances, a precursor sequence of a subject polypeptide sequence may be compared to the precursor of the reference sequence.

As used herein, a variant polypeptide is "based on" or "derived from" a parental (or wild-type) reference polypeptide if the variant polypeptide includes the same or substantially the same amino acid sequence as the parental polypeptide except for specified substitutions, deletions, insertions, chemical modifications, and the like. "Substantially the same" means that other than the specified substitutions, deletions, insertions, chemical modifications, and the like, the amino acid sequence of the variant does not include further substitutions, deletions, insertions, chemical modifications, or the like, that would significantly alter the properties of the parental polypeptide.

As used herein, "hybridization" includes the process by which a strand of nucleic acid joins with a complementary strand through base pairing, as well as the process of amplification as carried out in polymerase chain reaction (PCR) technologies. A nucleic acid encoding a variant α-amylase may exist as single- or double-stranded DNA or RNA, an RNA/DNA heteroduplex, or an RNA/DNA copolymer. As used herein, "copolymer" refers to a single nucleic acid strand that comprises both ribonucleotides and deoxyribonucleotides. The α-amylase encoding nucleic acid may be "optimized" to increase expression a specific organism by tailoring the nucleic acid to contain those codons which are preferentially utilized in translating native proteins in that organism.

As used herein, a "synthetic" compound is produced by chemical or enzymatic synthesis. Synthetic compounds include, but are not limited to, nucleic acids encoding α-amylase variants, preferably made with optimal codon usage for host organisms of choice for expression. A synthetic polypeptide or nucleic acid can also be prepared using in vitro techniques, such as in vitro transcription or translation, or PCR and the like.

As used herein, "transformed cell" includes cells, including both bacterial and fungal cells, that have been transformed by use of recombinant DNA techniques. Transformation typically occurs by insertion of one or more nucleotide sequences into a cell. The inserted nucleotide sequence may be a heterologous nucleotide sequence, i.e., is a sequence that is not naturally present in the cell that is to be transformed, such as a nucleic acid encoding a variant, fusion protein, or chimeric polypeptide.

As used herein, "operably-linked" means that the described components are in a relationship permitting them to function in their intended manner. For example, a regulatory sequence can be "operably-linked" to a coding sequence in such a way that expression of the coding sequence is achieved under conditions compatible with the regulatory sequence.

As used herein, "biologically active" refers to a sequence having a similar structural, regulatory or biochemical function as the naturally occurring sequence, although not necessarily to the same degree. For example, a biologically active α-amylase is a polypeptide with measurable α-amylase activity.

As used herein the term "starch" refers to any material comprised of the complex polysaccharide carbohydrates of plants. Starches generally comprise amylose and amylopectin with the formula $(C_6H_{10}O_5)_x$, wherein X can be any integer. The term "granular starch" refers to raw, i.e., uncooked starch, e.g., starch that has not been gelatinized.

As used herein the term "saccharification" refers to enzymatic conversion of starch to glucose.

The term "liquefaction" refers to the stage in starch conversion in which gelatinized starch is hydrolyzed to give low molecular weight soluble dextrins. The term "degree of polymerization" (DP) refers to the number (n) of anhydroglucopyranose units in a given saccharide. Examples of DP1 are the monosaccharides glucose and fructose. Examples of DP2 are the disaccharides maltose and sucrose. For purposes herein "comparable liquefaction processes" are those conducted under comparable conditions, preferably conditions standardized for temperature, pH, substrate concentration, calcium ion concentration and the like. Preferably comparable liquefaction processes are compared on an equal protein or equal activity units basis, however, is some embodiments, either protein, or activity units, or both may vary in comparable liquefaction processes. The skilled artisan will understand the bases on which liquefaction processes may be "comparable".

During liquefaction processes, the viscosity of the starch slurry is frequently used as a measure of the conversion of the starch into smaller DP units. Sometimes herein the expression "initial viscosity" is used. The skilled artisan will appreciate that this is a term of art, and what is intended is not literally the initial viscosity, but rather the peak viscosity which occurs for example at around the point of gelatinization of the substrate. Initial viscosity is used to distinguish from the "final viscosity" which is the viscosity of a substrate, e.g., starch slurry, at the conclusion of a liquefaction process. Thus, as is apparent from looking at a graph of the viscosity over the time-course of a liquefaction process, the initial or peak viscosity occurs not immediately, but after a certain passage of time, e.g., less than 50% of the overall time, and more preferably within about the first ⅓ or even ¼ or ⅕ of the total time of liquefaction. For example, in a liquefaction exemplified herein, the peak viscosity typically occurs within the first ten minutes, after which time the enzyme is added and the viscosity begins to drop. As the starch granules open up during the gelatinization process, the interior of the granules become more accessible to the amylase activity and more cleavage, resulting in a drop in viscosity.

As used herein the term "dry solids content" (ds) refers to the total amount of solids in a slurry, on a dry weight basis. Dry solids content and dry weight basis are usually expressed as the weight of the subject material as a percentage of the weight of the total dry material. The term "slurry" refers to a mixture containing insoluble solids in a liquid, typically water or a similar solvent. Starch or flour is frequently suspended in a water-based solution to form a slurry for testing amylases, or for liquefaction processes.

The term "dextrose equivalent" or "DE" is defined as the percentage of reducing sugar as a fraction of total carbohydrate. The term "degree of polymerization" or "DP" refers to the size of products of amylase degradation of starch. The higher the DP, the more complex the carbohydrate. α-amylases preferably produce products of low DP, e.g., DP2.

"Blend" or "enzyme blend" refers to a composition comprising a mixture of two or more enzymes providing therefore a combined catalytic activity that entails the activity of each of the enzymes present in the mixture. Enzyme blends need not have equal amounts of each of the two or more enzymes, but enzyme blends may be formulated on an equal protein, or equal activity basis, if desired. The combined catalytic activity may be merely additive or averaged, or may be antagonistic or synergistic. Preferred blends for use herein provide at least additive catalytic activity, and more preferably, synergistic catalytic effects.

For purposes herein, a "comparable liquefaction process" means a similar processes performed under controlled and specified conditions, (e.g., with respect to temperature, pH, calcium ion concentration, and substrate concentration) using a different or "control" amylase, and which can be compared to a subject liquefaction process.

As used herein, one "alpha amylase unit (AAU)" is the amount of bacterial alpha amylase activity required to hydrolyze 10 mg of starch per minute under specified conditions.

"SPEZYME® XTRA" is a commercially available enzyme preparation produced by Genencor, International, that includes as an active ingredient a variant of the *Geobacillus stearothermophilus* wild-type α-amylase that is truncated at the C-terminus (i.e., the C-terminal 29 residues). The specific activity is typically 14,000 AAU/g.

"SPEZYME® FRED" is a commercially available enzyme preparation produced by Genencor, International, that includes as an active ingredient an engineered variant of the *B. licheniformis* α-amylase having the substitutions M15T, H133Y, N188S, and A209V. The specific activity is a minimum of 17,400 AAU/g.

"SPEZYME® ETHYL" is a commercially available enzyme preparation produced by Genencor, International, that includes as an active ingredient a variant of the *Geobacillus stearothermophilus* α-amylase having an RG deletion (i.e., R179 and G180). The amylase polypeptide is processed to remove the C-terminal 29 residues. The specific activity is 6,700-7,300 AAU/g.

2. Abbreviations

The following abbreviations apply unless indicated otherwise:
AAU alpha amylase units
ATCC American Type Culture Collection
cDNA complementary DNA
CFU colony forming units
DE Dextrose Equivalent
DEAE diethylaminoethanol
DNA deoxyribonucleic acid
DNS 3,5-dinitrosalicylic acid
DP or DPn degree of polymerization (with n subunits)
ds dry solids
EC Enzyme Commission for enzyme classification
FDA Food & Drug Administration
FAO Food and Agriculture Organization of the United Nations
GLP Good Laboratory Practices
GMP Good Manufacturing Practices
HPLC High Performance Liquid Chromatography
HPAEC-PAD High-performance anion-exchange chromatography with pulsed amperometric detection
HS higher sugars (DPn, where n>3)
JECFA Joint FAO/WHO Expert Committee on Food Additives
kb kilobase
LAT *B. licheniformis* α-amylase
LU liquefaction units
MALDI-TOF Matrix-assisted laser-desorption ionization-time of flight mass spectrometry
mRNA messenger ribonucleic acid
mL milliliter
mt metric ton (1000 kg)
N Normal
M Molar
nC nano Coulombs
PCR polymerase chain reaction
PEG polyethyleneglycol
ppm parts per million
RO reverse osmosis
RT-PCR reverse transcriptase polymerase chain reaction
SDS-PAGE sodium dodecyl sulfate-polyacrylamide gel electrophoresis
SKBU/g ds α-Amylase Unit per gram of dry solids. One α-Amylase Unit dextrinizes 1.0 g of limit-dextrin substrate per hour under the conditions of the assay.
1×SSC 0.15 M NaCl, 0.015 M sodium citrate, pH 7.0
WHO World Health Organization
w/v weight/volume
w/w weight/weight
μg microgram
μL microliter

B. VARIANT α-AMYLASES

In a first of several aspects, variants of an α-amylase from *Bacillus stearothermophilus* are provided. The variants are based on modifications to the wild-type amylase sequence at position 181 or 182 of the mature protein, wherein the wild-type amino acid at positions 181 and 182, or both, are substituted. The substitutions for the wild-type amino acid at position 181 include Ala, Cys, Asp, Glu, Leu, or Pro, and substitutions for the wild-type amino acid at position 182 include Ala, Ser, or Pro. In one embodiment, the variant amylase has increased specific activity compared to the wild-type α-amylase, under specified assay conditions. In various embodiments, the variant has an improvement of about 10, 20, 30, 40, 50, 60, 70, 80, 85, 90, 95, 100%, or more in terms of specific activity. In other cases, the variant amylases have specific activity of 2-fold, 3-fold, 4-fold or more relative to the wild-type. This feature provides additional advantages, allowing less enzyme to be used in a given application, and minimizing issues with production capacity. Preferably, the variant has increased specific activity between about 50-90° C. In other embodiments, the variant has increased specific activity between about 65-85° C.

In some embodiments, the variant α-amylase has the amino acid sequence of SEQ ID NO: 2, 3, 4, 5, 6, 10, or 15. These sequences comprise single mutations or variations at position 181 of the wild-type amino acid sequence. In some embodiments, the wild-type/parental sequence is that of AmyS, the mutations or variations are at position I181, therein. Generally, a designation of the form "$X_1POSX_2$" indicates that the variant contain a varied amino acid sequence at position "POS", wherein the wild-type amino acid residue, $X_1$ is replaced with a different amino acid residue, $X_2$, wherein $X_1$ and $X_2$ are standard single letter codes for amino acids, and "POS" is any position within the primary amino acid sequence of the wild-type mature sequence. Thus, variants at I181 are amylase sequences wherein a wild-type sequence with an isoleucine at position 181 of the wild-type sequence is replaced with another amino acid. Presently preferred are I181P, I181A, and I181L variants. In other embodiments variants including I181C, I181D, I181E, and I181Y are useful. The variants I181F, I181G, I181H, and I181V are also contemplated.

In a preferred embodiment, the variant has the sequence of SEQ ID NO: 2, 3, or 10. Where the wild-type/parental sequence is that of AmyS, these mutations or variations correspond to I181I, I181A, and I181L, respectively. In one embodiment, when used in a liquefaction process, the amylase activity reduces the peak viscosity of a starch slurry relative to that of a comparable starch slurry liquefied with a corresponding wild-type α-amylase.

In some embodiments, the variant α-amylase has the amino acid sequence of SEQ ID NO: 16, 17, or 18. These sequences comprise single mutations or variations at position 182 of the wild-type amino acid sequence. In some embodiments, the wild-type/parental sequence is that of AmyS, the mutations or variations are at position G182, therein. Presently preferred are G182A, G181S, and G182P variants.

The variant does not have the sequence of other known α-amylases, for example those α-amylases disclosed in U.S. Pat. No. 6,939,703 by Van Der Laan and Aehle, U.S. Pat. No. 6,143,708 by Svendsen et al., or U.S. Pat. No. 5,830,837 by Bisgørd-Frantzen et al. Similarly, other known sequences are not encompassed by the variant amylases described herein, for example the sequences disclosed in *J. Biochem. Mol. Biol.* 40: 315-324 (2006) by Sajedi et al. are also specifically excluded. The α-amylase sequences provided in the public databases of the European Molecular Biology Laboratories (EMBL) or the National Center for Biotechnology Information (NCBI) more than one year prior to the filing date of this disclosure are also expressly excluded as sequences of the present α-amylase variants. Any of such known sequences can be individually excluded from the present compositions and method using a proviso.

The variant α-amylases that are encompassed by the present compositions and method possess the basic catalytic activity of α-amylases, which allows them to attack (i.e., hydrolyze) α-1,4 linkages of a substrate such as amylose and/or amylopectin of starch, converting it to dextrins of lower DP. In the process of doing so, the α-amylases reduces the viscosity and increases the dextrose equivalence (DE), making them useful for liquefying and dextrinizing starch, typically in slurries. α-amylases are also used for other starch degradation processes, e.g., desizing woven materials and cleaning processes where undesired starch must be removed.

A feature of the present α-amylase variants is that they demonstrate improved performance characteristics relative to the wild-type/parental amylase from which they were derived. In other embodiments, the variants have improved performance relative to other α-amylases such as AmyL or AmyS. In some embodiments, the variant amylases show improved application performance over convensional commercial enzyme preparation used for the same purpose.

The improved performance characteristics include improved stability, pH range, oxidation stability, and thermostability. In particular, the α-amylase variants provide better stability at high temperatures (e.g., 70-90° C.), and/or increased specific activity at high temperatures. The thermostable variant amylases provided herein are advantageous for use in high temperature liquefaction, as well as in other processes that employ or require elevated temperatures, such as cooking, baking or the like.

Another performance characteristic of the present variants is that they reduce the peak viscosity of a starch slurry. This benefits the liquefaction process by requiring less energy for mixing and allowing faster conversion of the starch to lower DP products.

C. COMPOSITIONS COMPRISING VARIANTS α-AMYLASES

Also provided are a variety of compositions comprises one or more α-amylase mutants having the catalytic activity of an α-amylase. The compositions include, for example, enzyme concentrates, enzyme blends, purified enzymes, partially purified enzyme products, food additives, and cleaning products containing the variant α-amylase.

In one embodiment, the composition includes a variant amylase as described or exemplified herein. Such compositions have a variety of uses. The compositions can also provide more than one amylase variant, or other amylases, or a combination thereof. The compositions can be highly purified or only partially purified. In certain embodiments, the compositions are standardized in terms of units of activity. The compositions can be provided in a variety of physical forms including liquids of various concentrations and purity, gels, cakes, semisolids, or solids. The compositions are amenable to any physical form, provided that measurable activity remains in the final composition. Thus, the compositions can be conveniently lyophilized, concentrated, frozen, spray-dried, or otherwise processed in a variety of known or useful manners. The compositions can be provided in standard sizes for certain commercial applications, or custom packaged, or provided in bulk containers of any type.

The compositions and enzyme blends can further comprise or be used in conjunction with one or more additional polypeptides. Preferably, the one or more additional polypeptides comprise at least one enzyme. Thus, any known enzyme can be used with the compositions or enzyme blends, or of course with the α-amylases themselves. Any of a variety of additional enzymes may be added to the compositions, enzyme blends, or α-amylases disclosed herein to provide further utility or convenience, as is desired by the skilled artisan. In various embodiments, the additional enzyme can comprise one or more of bacterial α-, or β-amylases, e.g., BBA, fungal α-amylases, e.g., CLARASE® L, or glucoamylase, isoamylases, isomerases, proteases, such as fungal and bacterial proteases, cellulases, lignases, hemicellulases, lipases, phospholipases, and cutinases. Compositions comprising one or more α-amylase variants as disclosed herein together with each other, or in a combination with any one or more of the foregoing are contemplated for use herein. As disclosed above, fungal proteases include, for example, any protein-degrading enzyme activities obtained from *Aspergillus* spp., such as *A. niger, A. awamori, A. oryzae; Mucor* spp., e.g., *M. miehei; Rhizopus* spp., and the like. β-amylases (EC 3.2.1.2) are exo-acting maltogenic amylases, which catalyze the hydrolysis of 1,4-α-glucosidic linkages into amylopectin and related glucose polymers, thereby releasing maltose. β-amylases have been isolated from various plants and microorganisms. See Fogarty et al., in PROGRESS IN INDUSTRIAL MICROBIOLOGY, Vol. 15, pp. 112-115 (1979). These β-amylases have optimum temperatures in the range from 40° C. to 65° C. and optimum pH in the range from about 4.5 to about 7.0. Contemplated β-amylases include, but are not limited to, β-amylases from barley SPEZYME® BBA 1500, SPEZYME® DBA, OPTIMALT™ ME, OPTIMALT™ BBA (Genencor International, Inc.); and NOVOZYM™ WBA (Novozymes A/S).

In one embodiment, a composition or an enzyme blend comprises one or more additional enzymes that is useful for liquefaction of a complex carbohydrate comprising amylose and amylopectin. In one embodiment, the additional enzyme is an α-amylase. Any known α-amylase can be used in connection with the amylases, compositions, or enzyme blends, including bacterial α-amylases, e.g., of from *Bacillus*, such as AmyL-, AmyS-, AmyQ-, or AmyM-type amylases, fungal amylases, or plant or animal amylases. Such compositions, or blends, when used in a liquefaction process, preferably reduce the peak viscosity of a starch slurry relative to that comparable starch slurry liquefied with a single enzyme, particularly the wild-type enzyme. In one embodiment, the compositions or blends comprising two or more enzymes reduce the peak viscosity of a starch slurry to at least the viscosity produced by any of the two or more enzymes when used alone, and also result in a final viscosity of the starch slurry at least as low as the final viscosity produced by any of the two or more enzymes when used alone.

The compositions in one embodiment are prepared or formulated for use as a food additive or as a processing aid suitable for use in food processes. A food-grade lyophilized composition comprising an α-amylase variant as disclosed herein is also provided. When prepared or formulated for use as a food additive or for use in food processes, the compositions must meet or exceed certain regulatory requirements. These requirements serve as a guide to the skilled artisan in preparing the compositions. Accordingly, the skilled artisan will appreciate that although the regulatory requirements may differ in various countries, generally the composition will be very low in heavy metal content, as well as low in lead and arsenic. Specifically, the total heavy metal content is preferably does not exceed about 40 ppm, and more preferably is less than about 30 ppm. The lead content of the compositions does not exceed about 10 pm, and more preferably is less than about 5 or 3 ppm. The arsenic content of the composition is less than about 3 ppm. The compositions are also negative for mycotoxin and antibacterial content, when tested be standard methods. The compositions are also clean with respect to their microbiological content, preferably being produced under GMP or GLP standards at a minimum when intended for food additive use or as food processing aids. In particular the total viable count will not exceed about $5 \times 10^4$ CFU per gram of composition. The compositions will preferably have a coliform count that does not exceed about 40 CFU per gram of composition. More preferably the count of coliforms will not exceed about 30 CFU per gram. Further, the compositions have no detectable *Salmonella* or *Shigella*, as measured by standard microbiological methods. Where the variant amylases are produced in host cells, the compositions will have less than 1 CFU of the host organism per gram.

Further, the compositions will possess a satisfactory standard of safety in terms of toxicity and the like. In one embodiment, the compositions produce no evidence of genotoxic potential in suitable in vitro assays. The compositions also show no evidence of toxic effects in acute and/or sub-chronic dosing studies in animals.

For purposes of food additive or food processing aids, the production is preferably standard, as for many commercially-used food enzymes. Thus, GMPs are used throughout the production process, meeting the requirements and specifications for food enzymes established for example by the FDA, or international authorities, e.g., Food Chemicals Codex (4th Edition, 1996), the Joint FAO/WHO Expert Committee on Food Additives (JECFA) in the Compendium of Food Additives Specifications, Vol 1, Annex 1 Addendum 9 (2001) (and earlier relevant Addenda). For example, the compositions comprising the α-amylase variants are produced using a process such as a fed-batch fermentation, e.g., a submerged fed-batch fermentation in an organism that is generally recognized as safe, or which has a long history of use for such purposes, for example for the production of food-grade enzyme preparations.

For some purposes herein, suitable host organisms include Gram-positive bacteria from the genus *Bacillus* including, for example, *B. stearothermophilus*, *B. subtilis*, *B. licheniformis*, *B. brevis*, and *B. amyloliquefaciens*. Others including *B. coagulans*, *B. circulans*, *B. lautus*, *B. lentus*, *B. thuringiensis*, and *B. alkalophilus* may also be useful. Other Gram-positive bacteria that may be useful for production of some of the compositions described herein include *Streptomyces lividans*, and *S. murinus*. Gram-negative bacteria, including *Escherichia coli* or a *Pseudomonas* species, may also be used to produce certain of the compositions provided herein.

Also provided herein are compositions comprising α-amylase variants that are useful to facilitate removal of a substrate for the enzyme (e.g., starch) from a variety of nonstarch (thus, nonsubstrate) materials, such as textiles, paper, glass, plastic, metal, canvas, porcelain, and the like. Because such materials are frequently removed during washing or cleaning processes, the compositions in one embodiment includes one or more soaps, detergents, cleaning agents, oxidants, or chelators. In one embodiment, the composition is a used a laundry detergent, in another it is a dishwashing detergent. The compositions, for these and other purposes described herein, may be formulated as gel. A variety of such gels are known in the art and provide certain advantages, for example, with respect to contact time and conditions for the enzyme to work on the substrate to be removed, in addition to an appealing and convenient usage form for consumers or users. The inclusion of standard cleaning agents, as well as detergents, soaps, oxidants, and/or chelators requires that the α-amylase activity be stable to the conditions found not only in the end-use, but in the more concentrated or extreme conditions found in the product itself.

D. CHARACTERIZATION OF THE VARIANTS α-AMYLASES

Enzymes such as the α-amylase variants provided herein can be characterized by a variety of methods and techniques known in the art. The nucleic acid and primary polypeptide sequences, are useful means of comparing and analyzing the amylases provided herein. Three dimensional structural modeling, and/or physical crystallization are also useful. Determination of specific activity is frequently used characterize enzymes. Enzyme activity under a variety of conditions of substrate, temperature, pH, calcium concentration and other factors can be assessed using standard assays known to the artisan skilled in this field, or by designing new assays based on known techniques of assaying amylases. Determining kinetic properties of the enzyme, including kinetic constants, such as $V_{max}$ or $K_m$ under specified conditions, is also useful for characterizing the variant amylases provided herein. Methods for determining the optimal pH for stability or for assay are known in the art, as are methods for determining the optimal calcium ion concentration for maximum activity, and conditions for maximal stability during storage of the α-amylase variants.

Applied characterization includes characterizing the enzyme activity in terms of the result produced under simulated processing conditions. Bench-top liquefaction processes, and the like can be used to measure or assess the performance of the variants under conditions that more closely approximate actual use conditions. Viscometry studies can help characterize the amylase's catalytic activity in terms of the peak viscosity reached during a process, or the final viscosity of a starch slurry degraded or treated with the amylase variant. In many useful embodiments, comparisons are made to wild-type amylase, to a control amylase, or to a commercial amylase used for similar conditions. Comparisons to other amylase variants are also useful for assessing relative the value or utility of particular enzymes.

Characterizing expression of the variant amylases in a host cell can be a useful characteristic, for example in determining the commercial potential of a process of making the amylase variants. To evaluate the expression of the variant α-amylases in a host cell, one can measure the expressed protein, the corresponding mRNA, or the enzyme activity. Suitable assays include Northern and Southern blotting, RT-PCR (reverse transcriptase polymerase chain reaction), and in situ hybridization, using an appropriately labeled hybridizing probe. Measurements of the amount of expression of the amylase produced in a particular host cell, the rate of expression, or the maximal recovery are all examples of useful characteristics related to expression of the variant amylases.

The α-amylase variants described herein can also exhibit extended half-life at a given temperature, relative to the AmyS or AmyL enzymes. In various embodiments, half-life can be increased by 10%, 20%, 30%, 40%, 50%, 60%, 70%, 80%, 90%, 100%, 200%, or more, particularly at elevated temperatures of about 55° C. to about 95° C. or more, particularly at about 75° C., 80° C., 85° C. or above.

In some embodiments, the specific activity of the α-amylase variants is improved relative to the wild-type sequence from which the variant is derived. Improvements in specific activity of about 10%, 20%, 30%, 40%, 50%, 60%, 70%, 80%, 90%, 100%, 200%, or even more can result in the variant amylases.

In one embodiment, the α-amylase variants provided herein have the same pH stability as a parent sequence, such as the AmyS enzyme. In another aspect, the variant amylases exhibit a greater range of stability to pH changes, or pH optimum or stable range is shifted to a desired range for the end commercial purpose of the enzyme. For example, in one embodiment, the variant amylase can degrade starch at about pH 4.5 to about pH 10.5. The α-amylase variant may have a longer half-life or higher activity (depending on the assay) relative to AmyS under identical conditions. The α-amylase variants also may have about 10%, 20%, 30%, 40%, 50%, 60%, 70%, 80%, 90%, 100%, 200% or longer half-life under identical pH conditions. In another embodiment, the α-amylase variants may have higher specific activity, as compared to a wild-type sequence, or parent enzyme, for example, AmyS, under identical pH conditions. The α-amylase variants provided herein may have any combination of desirable characteristics listed herein above.

E. POLYNUCLEOTIDES ENCODING THE VARIANT α-AMYLASES

In another of it several aspects, provided are polynucleotides that encode a variant of a *B. stearothermophilus* α-amylase as described herein. Because the encoded polypeptides are not found in nature, the polypeptides must be made by the hand of man, e.g., synthesized, or created for example, through a directed mutation and screening program. Specifically, the polynucleotides encode a polypeptide that comprises the wild-type amylase sequence except for a substitution at position 181 or 182 of the mature protein, wherein the wild-type amino acid at positions 181 and 182, or both, are substituted. The substitutions for the wild-type amino acid at position 181 include Ala, Cys, Asp, Glu, Leu, or Pro, and substitutions for the wild-type amino acid at position 182 include Ala, Ser, or Pro.

In various embodiments, the polynucleotide encodes a polypeptide that is a I181P, I181A, and I181L variants. In other embodiments, the polynucleotide encodes variants including I181C, I181D, I181E, and I181Y, or even I181G, I181H, and I181V.

The polynucleotide encodes a polypeptide that has the amino acid sequence of SEQ ID NOs: 2-18, preferably SEQ ID NOs: 2-6, 10, 15, and 17-19, and in some case SEQ ID NOs: 2, 3, 10, 16, and 18 in various embodiments. In particular embodiments, the encoded variant polypeptide has the sequence of SEQ ID NOs: 2 or 3.

In one embodiment, the polynucleotide is a genomic DNA, while in another embodiment, the polynucleotide is a cDNA. Due to the degeneracy of the genetic code, there are multiple polynucleotides provided in accordance with this disclosure that can encode the same polypeptide. Polynucleotides also include mRNAs that encode α amylase variants as provided herein.

In one presently preferred embodiment, the polynucleotide encoding the α-amylase variant polypeptide is optimized for expression of the variant polypeptide in a host cell from a microorganism or a plant by adapting the polynucleotide's composition to favor the those codons used preferentially in the host cell. Techniques for optimizing codon usage are known in the art and codon usage tables for various organisms are available in standard resources such as texts or practice manuals for biotechnology.

Also provided are vectors comprising the polynucleotides encoding the variant amylases. Any vector for maintaining a polynucleotide, producing quantities of a polynucleotide, manipulating a polynucleotide sequence, or for expressing a polynucleotide in vitro or in a host cell is contemplated for use herein. Examples of suitable vectors are provided in standard biotechnology manuals and texts, e.g., Sambrook et al., MOLECULAR CLONING: A LABORATORY MANUAL, 3$^{rd}$ ed., Cold Spring Harbor Laboratory Press, Cold Spring Harbor, N.Y. (2001).

In one embodiment, preferred vectors are useful for expression of the encoded polypeptide in a host cell, especially in a microbial cell, such as a bacterial cell, or in a plant cell. Expression vectors may be adapted for transient expression of the variant α-amylases, for example, to confirm catalytic and other properties prior to scaling up. Expression vectors for long-term use, and large scale production are preferably adapted for stable expression, for example by integration into the host cell chromosome, or by stable incorporation of a self-replicating polynucleotide sequence. In one embodiment, the vector, a DNA construct is transferred to a host cell by an expression vector that comprises regulatory sequences operably-linked to a coding sequence for the α-amylase variant.

Also provided are microbial cells, including yeast, fungi, or bacterial cells, comprising the vector comprising the polynucleotide that encodes the variant α-amylase. In one embodiment, the vector is an expression vector suitable for expression of the encoded polypeptide in the host cell. In another embodiment, a plant cell is provided which comprises a plant expression vector. Vectors for expression in various host cells are known in the art and contain required regulatory sequences, such as promoters and the like, to facilitate expression of an encoded polypeptide. Exemplary promoters for use in Bacillus include the promoters from the amylase genes in AmyL, AmyQ, AmyM, or AmyS, as well as the promoters from xylA and xylB genes in B. subtilis. In one embodiment, the expression vector contains one or more strong promoters, either constitutive or inducible for expressing or over-expressing the encoded polypeptide. In another embodiment, the polynucleotide includes sequences for post-translational modification of the peptide, such as transporting the expressed polypeptide out of the cell, or to a specific compartment within the host cell, to facilitate production, isolation, or purification of the polypeptide from the host cell. For example, the polynucleotides can include one or more sequences such that the variant amylase is initially produced with a heterologous polypeptide attached to one end, such as a signal peptide from B. lichenformis to promote secretion of the expressed protein from a bacterial host cell. The polynucleotide may also include sequences such that the variant amylase is initially produced with a "purification sequence," i.e., a sequence to facilitate purification of the expressed protein, wherein the "purification sequence" is cleaved during purification.

Where the host cell is a plant, it is contemplated that in one embodiment the plant is a crop plant that is used for starch production. The amylase variant can be overproduced in the plant. The amylase variant can be overproduced and compartmentalized with that part of the plant used for starch storage, e.g., the seed. Thus, the plant can be harvested, the starch can be isolated and the α-amylase variant will be co-purified with the starch. This embodiment is particularly useful where the plant is to be used for alcohol fermentation, especially for example, for fuel ethanol.

In one embodiment, the host cell is from an organism acceptable for the production of food processing aids or food additives. Presently, host cells that are from Bacillus, especially B. lichenformis, B. subtilis, or B. stearothermophilus are preferred. Suitable plasmids for use in bacterial cells including vectors for self-replication in Bacillus are known in the art.

F. METHODS OF MAKING AND USING THE VARIANTS α-AMYLASES

Provided in accordance with another aspect of the disclosure herein are methods of producing the variants of B. stearothermophilus α-amylases. In one embodiment, the method provided produces a composition comprising at least one variant of a wild-type B. stearothermophilus α-amylase as described hereinabove. The variant amylase has measurable α-amylase activity. The method comprises utilizing a host cell as provided herein for a fermentation process wherein at least one variant amylase is expressed. After expression, the expressed variant amylase molecule is at least partially purified, thereby producing a composition comprising a variant α-amylase. In one embodiment, the expressed variant comprises a variant at position 181 or 182 of the mature wild-type protein, wherein the wild-type amino acid at positions 181 and 182, or both, are substituted, the substitution of the wild-type amino acid residue at position 181 including Ala, Cys, Asp, Glu, Leu, or Pro, and the substitution of the wild-type amino acid residue at position 182 including Ala, Ser, or Pro, respectively. In one embodiment, the variant has improved or increased specific activity as compared to a corresponding wild-type α-amylase, under specified assay conditions.

The host cell is from a Bacillus spp. in one embodiment. The fermentation process can be of any type, although fed-batch fermentation processes, such as submerged fed-batch fermentation, are useful herein.

The methods provided further comprise the step of further purifying the variant amylase in certain embodiments, to make a purified composition showing no evidence of genotoxic potential in in vitro assays; and no evidence of toxic effects in acute and sub-chronic dosing studies in animals. Such compositions are useful as food processing aids, or in some cases, as direct food additives.

The method produces a purified or partially purified composition that comprises not more than 40 ppm total heavy metals, not more than 5 ppm arsenic, not more than 10 ppm lead, not more than $5 \times 10^4$ total viable organisms (CFU/g), not more than 30 coliforms (CFU/g), and no detectable Salmonella, mycotoxins or antibacterial activity by standard tests.

In various embodiments, the methods are also useful for making partially purified or purified compositions that comprise more than one α-amylase activity, and in some embodiments further comprise at least one other enzyme activity. In one embodiment, the purified or partially purified composition comprises at least one other enzyme activity useful in a liquefaction process. The composition, whether purified or partially purified, when used in a liquefaction process, reduces the peak viscosity of a starch slurry relative to the peak viscosity of a comparable starch slurry liquefied with a single enzyme.

Also provided are methods using the compositions comprising the α-amylase variants. Methods of liquefying a complex carbohydrate, such as a starch slurry, are specifically provided. The methods comprise making a slurry comprising the complex carbohydrate, heating the slurry to an acceptable temperature for liquefaction, adding a composition comprising at least one α-amylase variant as provided herein, to the slurry, and incubating the slurry with the composition for a time and at a temperature sufficient to liquefy the complex carbohydrate. In a preferred embodiment the complex carbohydrate is a starch. As used herein "liquefy" does not mean that every available substrate linkage is cleaved, rather it means that the complex carbohydrate is at least partially hydrolyzed, as evidenced by a measurable reduction in final viscosity, an increase in the DE of the slurry, the release of low DP fragments/products, or another measure of an increase in reducing groups, dextrins, or α-maltose units.

In one embodiment of the method of claim, the substrate, i.e., the complex carbohydrate, is a starch, amylase, or amylopectin. The temperature of the liquefaction method can range from room temperature to over 100° C., but more preferably is about 50° C. to about 95° C. The liquefaction can entail a complex temperature curve over time, for example, the reaction may start at a low temperature and be increased by methods known in the art to the desired end temperature. The temperature may also be reduced after a specific amount of time, or after a desired end-point in reached in terms of viscosity, DE value, or another measure of liquefaction. The skilled artisan will thus appreciate that the method need not entail a specific temperature for a particular duration, provided that the amylase activity can function at the temperature and under the conditions provided. Other conditions that impact the activity include the pH and the calcium ion concentration, in addition to the presence or absence of inhibitors or the like.

The slurry comprises about 20-40% starch on a dry-weight basis in one embodiment, in another, the slurry comprises between about 30 to about 36 or 37.5% starch. Lower amounts of starch can be used, but may limiting in terms of economic considerations. Maximum viscosity and related factors, such as required power inputs for mixing may limit the maximum amount of starch to be used in the slurry. The skilled artisan will appreciate the practical considerations in making the starch slurry.

In one embodiment, the liquefaction is part of a fermentation. The inventors have discovered that the properties of the amylase variants disclosed herein, including those having the amino acid sequence of SEQ ID NOs: 2 or 3, are very useful in processes for fermentation of starches, because they can substantially decrease the peak viscosity of the starch slurry relative to that (the peak viscosity) of a comparable slurry treated with the wild-type enzyme from which the variant was derived, or treated with a currently-available commercial enzyme preparation. The fermentation is used to produce a food product, a food additive, a fuel, or a fuel additive in some embodiments. In preferred embodiments, fermentation is for a fuel or fuel additive that is an alcohol, preferably ethanol or another lower alcohol.

The skilled artisan will appreciate that, the more the viscosity is reduced, the further the starch is liquefied, the greater the production of dextrins (or the higher the DE of the resultant liquefied starch). Thus in one embodiment, the peak viscosity is reduced by at least 10, 20, 25, 30, 40, or even 50% or more relative to the peak viscosity of a comparable slurry liquefied by a wild-type enzyme from which the variant was derived, or treated with a currently-available commercial enzyme preparation.

Provided herein are methods of cleaning a surface to remove an unwanted or undesired starch residue. The methods comprise the steps of providing a surface that has a starch residue to be removed, contacting the surface with a composition that comprises one or more variant α-amylases, for a time and at a temperature sufficient, and under conditions permissive to result in removal of the starch residue. The surface can be on any material; for example, it can be on a dish, plate, glass, etc., or it can be on clothing or fabric. It can also be for example a counter-top or work surface, or a commercial vessel of any type that must be periodically or regularly cleaned.

In one embodiment, the composition used in the method comprises at least one other enzyme, for example one or more of a protease, a lipase, an additional amylase, or a combination thereof. In another embodiment, a step of rinsing or bulk removal of residue is implemented prior to the contacting step. Such a step removes bulk starch from the cleaning process to enable the enzyme to work on the remaining, and more difficult to remove, substrate. The method of cleaning can be conducted at any temperature, but preferably the temperature during the contacting step reaches at least 50-90° C. In one embodiment, the method comprises a step of sterilizing the surface, or steam treating the surface after the residue is removed. The composition further comprises at least one detergent, oxidant, chelator, or a combination thereof in several embodiments.

Also provided herein are methods of treating a woven material using the α-amylase variants described herein. Methods of treating woven materials, such as fabrics, with amylases are known in the art. The methods provided can improve the feel and/or appearance of a woven material, such as a textile or a fabric. The methods comprise contacting the woven material with a liquid comprising an α-amylase variant or a composition comprising a variant in accordance herewith. In one embodiment, the woven material is a fabric or textile. In another embodiment, the woven material is treated with the liquid under pressure. The liquid is generally an aqueous solution.

The methods are typically applied during or after a weaving process, e.g., the weaving of a fabric or textile. Alternatively, the method is used during a desizing stage, or during one or more additional steps further processing the woven material. The methods are useful because during weaving processes, the materials (e.g., threads) are exposed to considerable mechanical strain. Prior to the weaving process, particularly on commercial looms, the materials to be woven are often coated with a "sizing" comprising starch or starch derivatives, to increase their tensile strength and to prevent breaking. The variant amylases provided herein can be applied during or after weaving to remove such sizing starch or starch derivatives.

The α-amylase variants provided herein can be used alone or with other desizing chemical reagents, such as detergents and/or desizing enzymes to desize woven materials such as fabrics, including cotton and cotton-containing fabrics.

The α-amylase variants disclosed herein also have application for enzymatic finishing methods have been developed for clothing, for example, in the manufacture of denim jeans. The action of amylolytic enzymes to provide softness to the fabric and make the cotton more accessible to the subsequent enzymatic finishing steps (e.g., to achieve a stone-washed appearance).

G. ENZYME BLENDS AND KITS, AND METHODS OF USING THE SAME

Also provided herein are enzyme blends comprising at least a first and a second α-amylase. When each of the amylases is used alone in comparable liquefaction processes, the first α-amylase has a catalytic activity that results in a final viscosity lower than the second α-amylase. However, the catalytic activity of the first amylase results in a peak viscosity that is higher than the corresponding catalytic activity of the second α-amylase. Surprisingly, the enzyme blend provides combined catalytic activity that, when used in a liquefaction process, results in a final viscosity about the same as that resulting from the first α-amylase when used alone in a comparable liquefaction process. The blend also provides a peak viscosity substantially less than that resulting from the use of the second α-amylase alone in a comparable liquefaction process. As used herein "comparable liquefaction processes" comprise specified conditions of temperature, pH, calcium ion concentration, and substrate concentration.

As above for the composition comprising the α-amylases, the enzyme blends can further comprise or be used in conjunction with one or more additional polypeptides, such as, at least one enzyme. The skilled artisan will appreciate that any known enzyme can be used with the enzyme blends disclosed herein. Any of a variety of additional enzymes can be added to the enzyme blends to enhance utility or convenience, as is desired by the skilled artisan. The additional enzyme can comprise an enzyme that has starch- or carbohydrate-modifying activity, including debranching enzymes, maltogenic enzymes, and the like. For example, one or more of bacterial α-, or β-amylases, e.g., BBA, fungal α-amylases, e.g., Clarase® L, or glucoamylase, isoamylases, or isomerases may be used herein. Other enzymes that are contemplated for use herein include proteases, such as fungal and bacterial proteases, cellulases, lignases, hemicellulases, and cutinases, as well as lipases, and/or phospholipases. Enzyme blends comprising one or more additional α-amylase variants as disclosed herein, or other amylase activities, together with each other, or in a combination with any one or more of the foregoing are expressly contemplated for use herein. As disclosed above, fungal proteases include, for example, any protein-degrading enzyme activities obtained from *Aspergillus* spp., such as *A. niger, A. awamori, A. oryzae; Mucor* spp., e.g., *M. miehei; Rhizopus* spp., and the like. β-amylases (EC 3.2.1.2) are exo-acting maltogenic amylases, which catalyze the hydrolysis of 1,4-α-glucosidic linkages into amylopectin and related glucose polymers, thereby releasing maltose. β-amylases have been isolated from various plants and microorganisms. See Fogarty et al., in PROGRESS IN INDUSTRIAL MICROBIOLOGY, Vol. 15, pp. 112-115 (1979). These β-amylases have optimum temperatures in the range from 40° C. to 65° C. and optimum pH in the range from about 4.5 to about 7.0. Contemplated β-amylases include, but are not limited to, β-amylases from barley SPEZYME® BBA 1500, SPEZYME® DBA, Optimalt™ ME, Optimalt™ BBA (Genencor International, Inc.); and Novozym™ WBA (Novozymes A/S). Examples of other enzymes of various classes or activities have been commercialized and are known in the art, and suitable for use herein. In one embodiment, other enzymes that have specifically been formulated as food processing aids or as food additives are use in connection with an enzyme blend or other composition disclosed herein.

In one embodiment, an enzyme blend comprises one or more additional enzymes that are useful for liquefaction of a starch or other complex carbohydrate comprising amylose and/or amylopectin. In one embodiment, the additional enzyme is an α-amylase. Any known α-amylase can be used in connection with the amylases, compositions, or enzyme blends provided herein, including bacterial α-amylases, e.g., from any *Bacillus* spp., such as AmyL-, AmyS-, AmyQ-, or AmyM-type amylases, fungal amylases, or plant or animal amylases. Such blends or compositions, when used in a liquefaction process, preferably reduce the peak viscosity of a starch slurry relative to that comparable starch slurry liquefied with a single enzyme, particularly the wild-type enzyme. In one embodiment, enzyme blends comprising two or more enzymes reduce the peak viscosity of a starch slurry to at least the viscosity produced by any of the two or more enzymes when used alone, and also result in a final viscosity of the starch slurry at least as low as the final viscosity produced by any of the two or more enzymes when used alone.

Also provided is a method of liquefying a starch slurry comprising making a slurry comprising the starch, heating the slurry to an acceptable temperature for liquefaction, adding to the slurry an enzyme blend above comprising first and second α-amylases as described above, and incubating the slurry with the enzyme blend for a time and at a temperature sufficient to liquefy the starch slurry. The final viscosity of the slurry is about as low as that resultant from the use of the first α-amylase alone in a comparable liquefaction process, and the peak viscosity of the slurry is lower than that resultant from the use of the second α-amylase alone in a comparable liquefaction process. In one embodiment, the amount of enzyme blend added results in the addition of less of each of the first and second α-amylases than the corresponding amounts of the first and second α-amylases, respectively, added, when each is used alone in a comparable liquefaction process. The amount of each of the first and second α-amylases, respectively, is about half the corresponding amount added when each is used alone.

Also provided are kits of parts (i.e., kits) comprising a variant amylase. In one embodiment, kits for facilitating liquefaction of a starch slurry are provided. The kits include at least one of: a variant α-amylase as described herein, a composition comprising a variant amylase as described herein, a food-grade lyophilized composition as described herein, or an enzyme blend as described herein; and instructions for use of the kit in the liquefaction of a starch slurry.

Also provided are kits for practicing the foregoing methods of cleaning a starch residue from a surface, and for treating a woven material to remove a coating comprising starch or a starch derivative. The kits include at least one α-amylase variant as described herein, or one composition or enzyme blend as described herein, along with instructions for practicing the corresponding methods.

Further provided are methods of producing ethanol using the α-amylases, compositions, or enzyme blends disclosed herein. The methods comprise liquefying a starch slurry with one or more of: (a) a variant α-amylase from *Bacillus stearothermophilus*, wherein the amino acid at least at positions 181 and 182, or both, of said α-amylase are substituted relative to a wild-type α-amylase from *Bacillus stearothermophilus*, the substitution for the wild-type amino acid residue at position 181 including Ala, Cys, Asp, Glu, Leu, or Pro, and the substitution for the wild-type amino acid residue at position 182 including Ala, Ser, or Pro, respectively; (b) a composition comprising said α-amylase; (c) a food-grade lyophilized composition comprising said amylase; or (d) an enzyme blend comprising said amylase and a second amylase, said α-amylase having a catalytic activity that, when used in a liquefaction process, results in a final viscosity lower than, but a peak viscosity higher than, a corresponding catalytic activity of the second α-amylase, when each amylase is used alone in comparable liquefaction processes. After the addition of the enzyme, the resultant liquefied starch slurry is fermented with one or more organisms capable of producing ethanol, under conditions and for a time suitable for the production of ethanol in the fermentation. The skilled artisan will appreciate that any of a variety of organisms can be used to produce ethanol by fermentation of such a liquefied carbohydrate. Preferably, the resultant ethanol is at least partially purified, e.g., by any of a variety of methods known in the art, such as by distillation and condensation.

The skilled artisan will appreciate that certain organism selected for fermentation may provide higher yields or more efficiently ferment the carbohydrate if the slurry is further enzymatically processed or converted, for example to even smaller DP polymers—e.g., sugar monomers such as glucose, or a combination glucose and fructose. Thus, in one embodiment, the method comprises the optional step of adding one or more additional enzymes to the liquefied starch slurry to further effectuate the production of ethanol during the fermenting step. Such enzymes include amylases, for example maltogenic amylases or glucolytic amylases, isomerases, or even proteases or lipases. In one embodiment, the ethanol is purified sufficiently to be useful as a food or beverage, food additive, or fuel or fuel additive.

All references cited above are herein incorporated by reference in their entirety for all purposes. The working examples provided below are provided to further describe and illustrate certain aspects of the variants of the α-amylases, and thus should not be construed to be limiting.

EXAMPLES

Example 1

**Thermostability of α-Amylase Variants Based on a *Bacillus stearothermophilus* α-Amylase Sequence**

A library AmyS α-amylase variants having substitutions at position 181 were screened for thermostability relative to two controls, i.e., the parent α-amylase, AmyS, (from *Bacillus stearothermophilus*) and an commercial enzyme preparation, SPEZYME® ETHYL (Genencor International, Palo Alto, Calif.; described above). The library was generated by standard techniques. Certain variants, including the I181K, I181N, I181Q, and I181W were not represented in the library. Each variant in the library was prepared and screened for thermostability. Protein determinations were made on purified or plate samples. In all assays, an equal amount of α-amylase protein was added to the reaction.

Either plate or purified variants were diluted to a protein concentration of approximately 20 ppm using pH 5.6 malic acid buffer. The substrate consisted of 15% corn starch suspended in the same buffer. 400 μl of the starch suspension in reaction tubes was equilibrated to 70° C. for 2.5 minutes. 7 μL of the diluted enzyme was then added to the equilibrated starch suspension to a final protein concentration of about 0.35 ppm. The reaction mix was then placed into a pre-heated 85° C. shaking heating block and mixed at 300 rpm.

At the predetermined incubation time (20 minutes), the reactions were stopped by the addition of 50 μL of 125 mM NaOH. The reaction tubes were then spun and the supernatant was diluted 10-fold into 10 mM NaOH, for analysis for DP profile by HPAEC-PAD. The activity was calculated for each enzyme tested, the percent activity remaining for each enzyme was calculated based on the activity of that enzyme not subjected to the 85° C. thermal challenge.

Results:

The results of the above assay are shown in FIG. 1. The height of the bars reflects the percent residual activity (Y-axis) after incubation at 85° C. for twenty minutes. Each bar is identified by a letter that corresponds to the one-letter abbreviation of the amino acid residue that was substituted for the isoleucine naturally present in the AmyS α-amylase at position 181. Where no value is present (i.e., the height of the bar is zero), the variant corresponding to that substitution was not tested. The bar labeled "Z" represents the wild-type AmyS α-amylase. The bar labeled "$" represents a comparative control using the commercial enzyme preparation, SPEZYME® ETHYL (Genencor International).

A number of variants showed improved thermostability compared to wild-type AmyS. Of the variants, I181P, I181A, and I181L had the highest activity remaining after the thermal challenge. The error bars for I181P and I181A indicate that the difference is significant. Other variants, including I181C, I181D, I181E, and I181Y, on average, showed at least numerically increased thermostability as indicated by the activity remaining after the thermal challenge. The variants I181F, I181G, I181H, and I181V all appeared to have thermal stability comparable to the wild-type/parent enzyme, given the overlap of the error bars.

Example 2

Activity Profiles of Variant Vs. Commercial Enzyme Preparations

The activity profiles of two commercial enzymes were compared to that of the variant that demonstrated the greatest thermostability in the initial screen. Protein concentrations for purified samples and samples from plates were initially determined and all amylases were tested at equal protein concentrations.

Either plate or purified α-amylase variants were diluted to a protein concentration of approximately 20 ppm using pH 5.6 malic acid buffer. The substrate consisted of 15% corn starch in the same buffer. 400 μl of the starch suspension substrate in reaction tubes were equilibrated to 65° C. for 2.5 minutes. Diluted enzyme (10 μL) was added to the equilibrated starch suspension to a final protein concentration of about 1 ppm. The reaction mix was incubated for 5 minutes then placed into a pre-heated 85° C. shaking heating block and mixed at 300 rpm. At predetermined time intervals the reactions were quenched with 50 μL of 125 mM NaOH. The reaction tubes were then spun and the supernatant was diluted 10 fold into 10 mM NaOH for DP profile analysis by HPAEC-PAD, a commonly used technique for the chain length analysis of amylopectin.

Initial samples were taken after 5 minutes at 65° C. After ramping the temperature from 65° C. to 85° C., further samples were taken at 5, 15, and 30 minutes. Total area from DP2 to the end of the HPLC run was integrated, and the area was divided by the total protein and reaction time. For the high temperature incubation, the 5-minute reaction provides an indication of how quickly the enzyme begins to break down the substrate; the 15 minute reaction provides an indication of the enzyme's thermal activity, and the 30 minute provides an indication of the enzyme's thermal stability.

Figure 2:
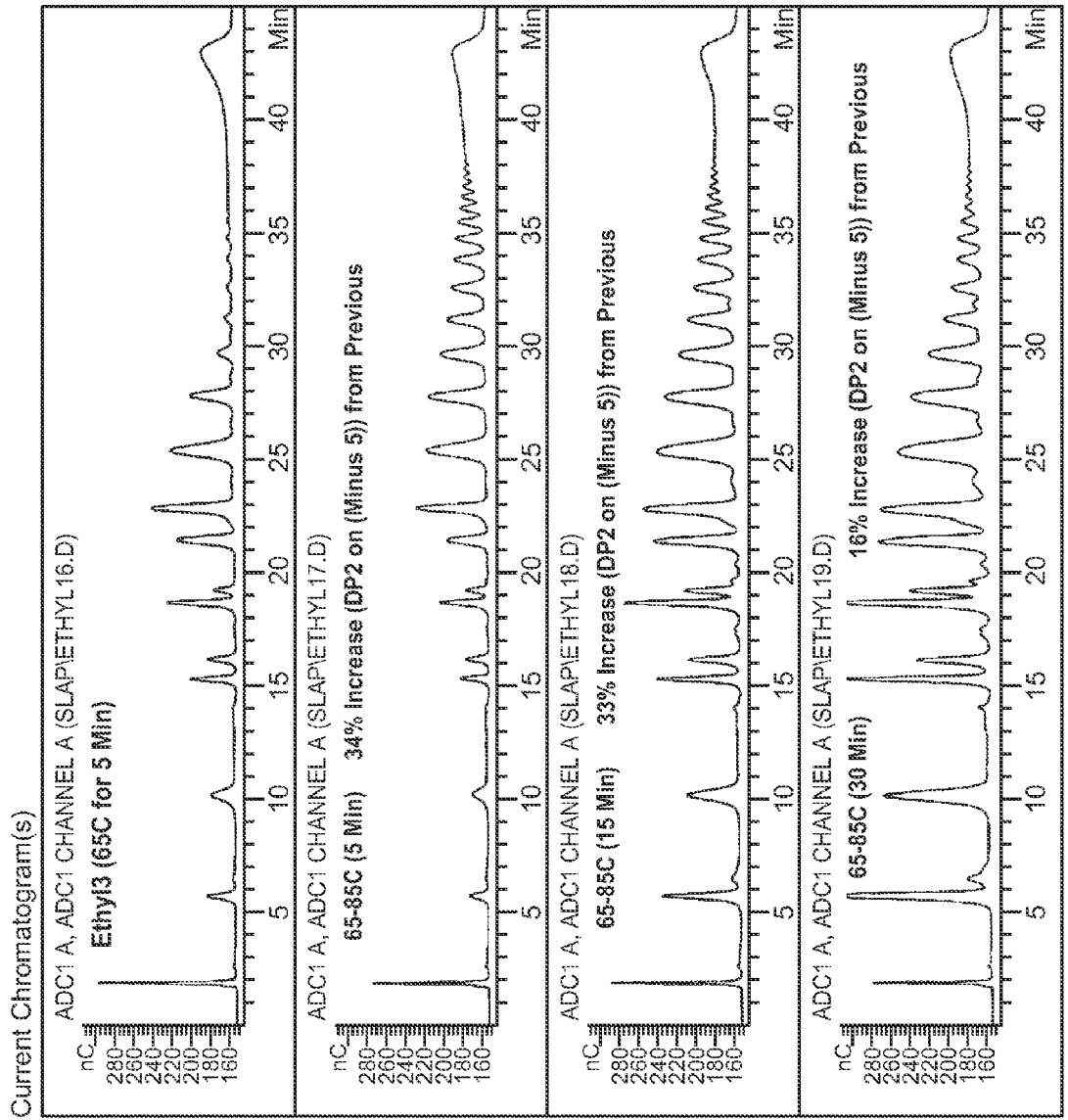
FIG. 2 shows the results of starch hydrolysis reaction (liquefaction) using the amylase SPEZYME® ETHYL. Panel A: HPLC Chromatogram of sample removed after 5 minute incubation at 65° C. Panels B, C, D: HPLC Chromatogram of sample removed 5', 15' and 30', respectively, after ramping the temperature from 65° C. to 85° C.
Figure 3:
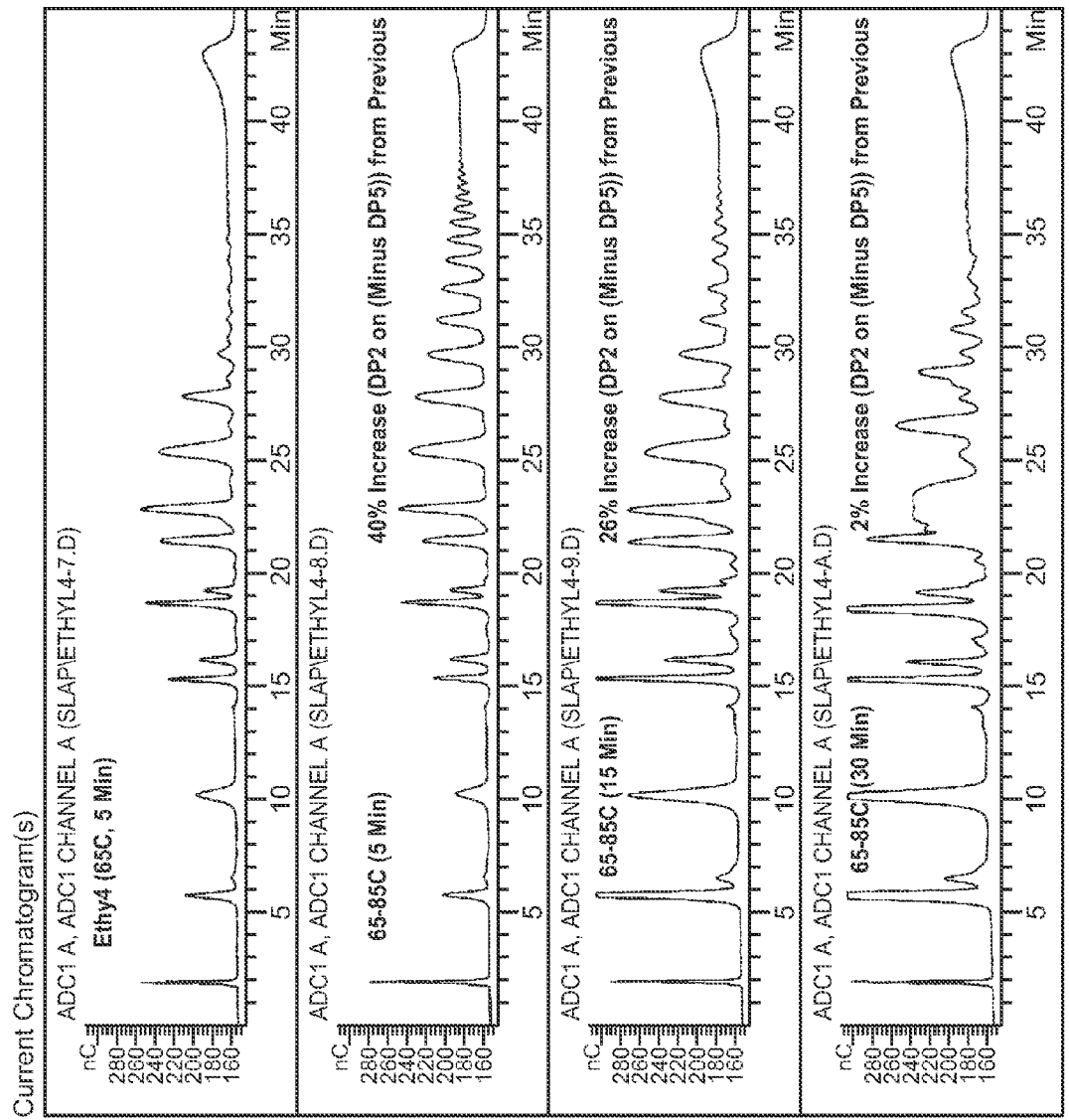
FIG. 3 shows the results of starch hydrolysis reaction using the amylase, SPEZYME® XTRA. Panel A: HPLC Chromatogram of sample removed after 5 minute incubation at 65° C. Panels B, C, D: HPLC Chromatogram of sample removed 5', 15' and 30' respectively after initiating ramping the temperature from 65° C. to 85° C.
Figure 4:
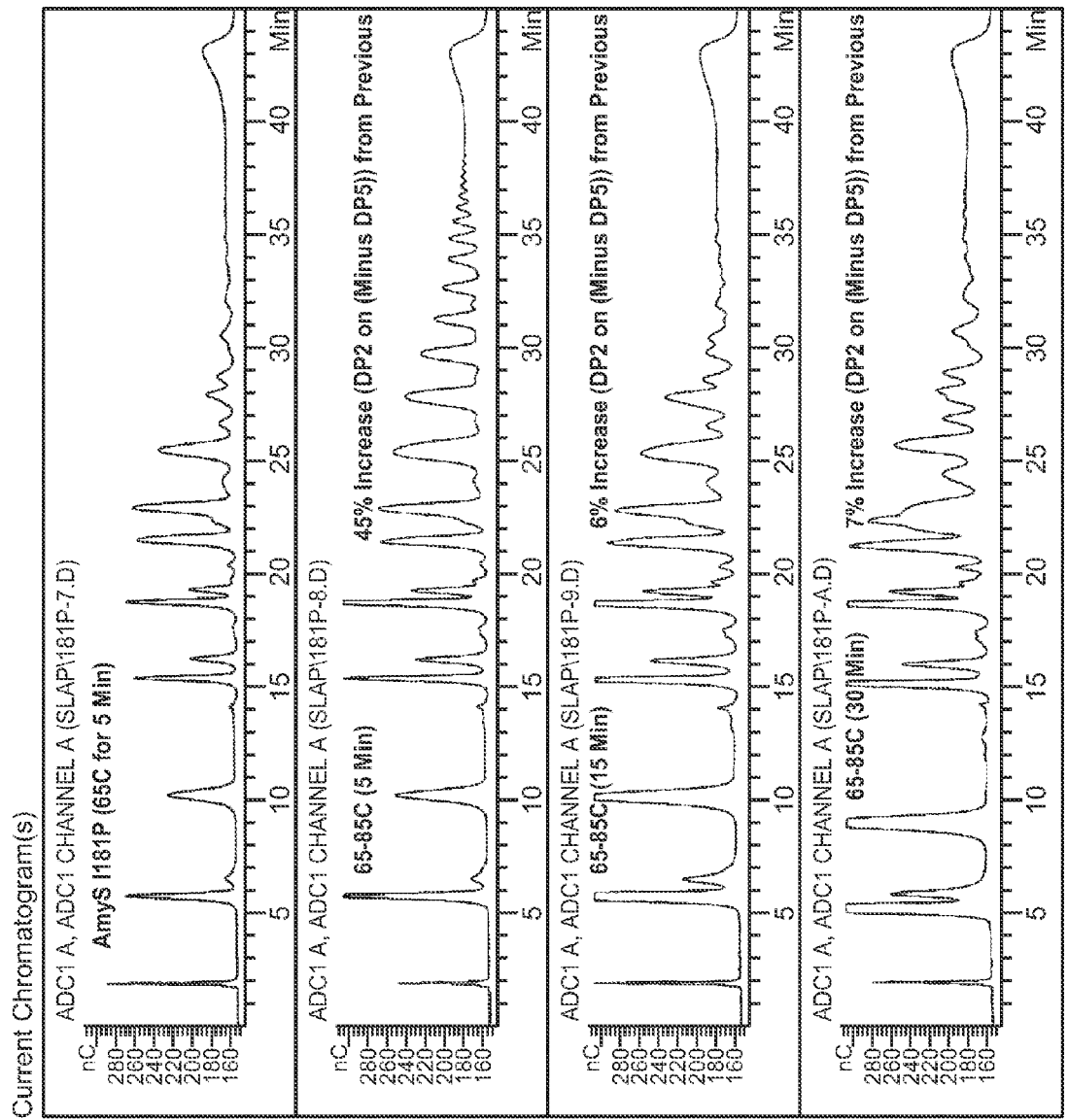
FIG. 4 shows the results of starch hydrolysis reaction using variant α-amylase AmyS I181P (SEQ ID NO:3). Panel A: HPLC Chromatogram of sample removed after 5 minute incubation at 65° C. Panels B, C, D: HPLC Chromatogram of sample removed 5', 15' and 30', respectively, after ramping the temperature from 65° C. to 85° C.

Results:

The results are shown in FIGS. 2, 3, and 4. The Y-axis on each chromatograph indicates the quantitative detection of the analyte by pulsed amperometric detection (PAD), expressed in nano Coulombs (nC). The X-axis represents the time of the elution from the column.

FIG. 2 shows the results for a commercial enzyme preparation, SPEZYME® ETHYL (Genencor International). As can be seen from Panels A-D, the enzyme activity continued to release lower DP fragments from the slurry over the time course of 30 minutes, as indicated by the increase in faster eluting peaks from 5 to 15 to 30 minutes of incubation. The 30-minute sample (Panel D) showed a 16% increase in DP2 fragments over Panel C (15 minutes), which showed a 33% increase in DP2 fragments over Panel B (5 minutes). Panel B showed a 34% increase in DP2 fragments over Panel A (65° C. incubation only).

FIG. 3 shows the results for another commercial enzyme preparation, SPEZYME® XTRA (Genencor International; described above). This enzyme acted more quickly initially; however, it appeared to be less thermostable, as the rate of increase in release of lower DP fragments continually dropped (e.g., Panel D versus Panel C). The 30-minute sample (Panel D) showed a 2% increase in DP2 fragments released over the 15-minute sample (Panel C), which showed a 26% increase over the 5 minute sample shown in Panel B. Panel B showed a 40% increase in DP2 fragments released over the sample incubated at 65° C. for 5 minutes.

FIG. 4 shows the results for the AmyS variant I181P. The variant enzyme activity provided a faster initial release of lower DP fragments, indicating that the variant has a very rapid initial activity. Compared to the initial sample (5 minutes at 65° C.), there was 45% increase after 5 minutes at 85° C. (Panel B). After 15 minutes (Panel C), there was a further 6% increase in the amount of DP2 fragments released. From Panel C to Panel D (30 minutes), there was a further 7% increase in the DP2 fragments released. It is unclear whether the reduced increase from Panel B to C to D is a result of thermal inactivation or a slowing in the cleaving of the substrate due to some other factor, such as the substantial early cleavage (and thus, loss) of the substrate, or perhaps due to other factors such as product inhibition. The initial rate of starch degradation is a very important factor for a commercial product, and the AmyS I181P variant demonstrated a high rate of initial degradation.

Figure 5:
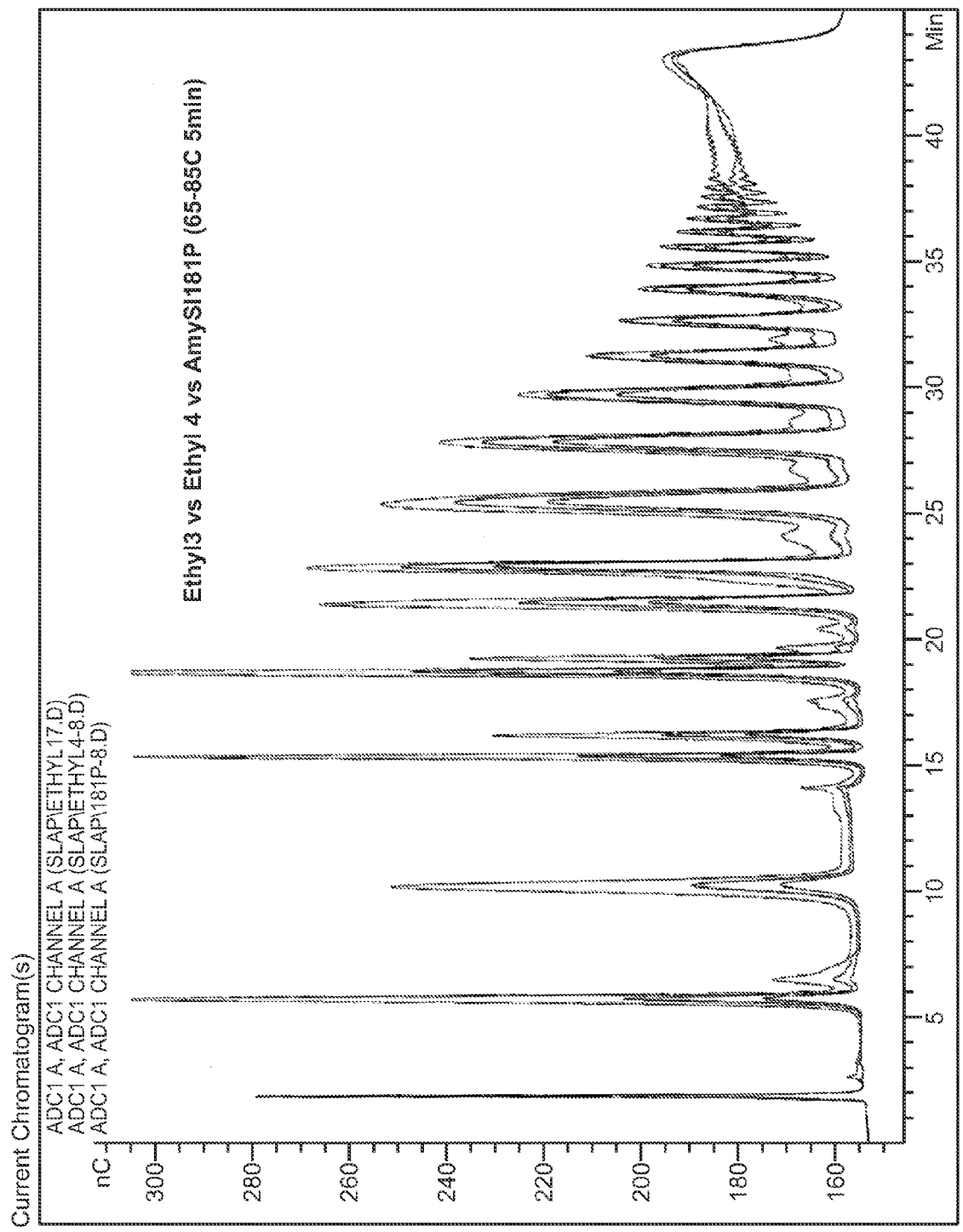
FIG. 5 shows a side-by-side comparison of Panels B from FIGS. 2, 3, and 4.

FIG. 5 shows a side-by-side comparison of the information shown in Panel B of each of FIGS. 2, 3, and 4. This time point represents 5-minutes incubation after initiating the ramping of temperature from 65° C. to 85° C., and provides a useful assessment of an enzyme's ability.

As in FIGS. 2, 3, and 4, the Y-axis provides quantitative results of detection using pulsed amperometric detection, expressed in nano Coulombs (nC), and the X-axis represents the elution time in minutes. The variant has a different activity profile and generally outperformed either of the commercial enzymes in terms of degrading the substrate to release the lower DP products, e.g., DP2 fragments.

Example 3

Viscometry of Variants of AmyS Compared to a Commercial Enzyme Preparation

This example shows that the present AmyS variants demonstrate altered performance compared to other α-amylases, including commercial preparations. Such altered performance generally included altered thermostability, altered rate of hydrolysis, and altered specific activity. Other altered performance features that were observed during hydrolysis of starch slurries (e.g., liquefaction) included altered peak viscosity and/or altered final viscosity.

Figure 6:
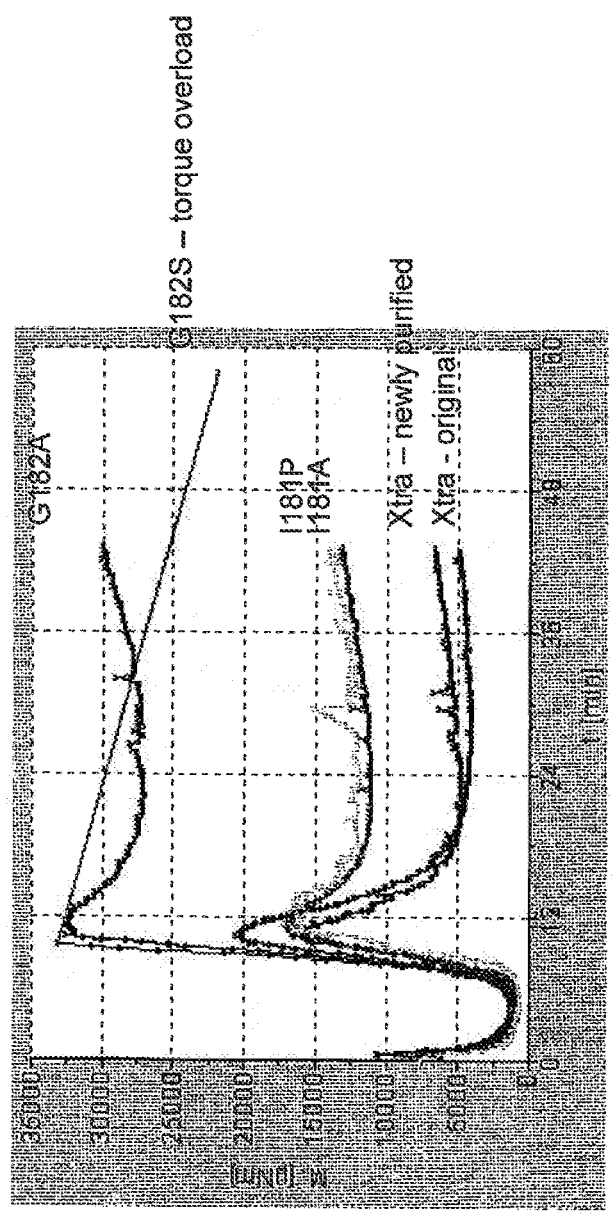
FIG. 6 shows a comparison of variant α-amylases with SPEZYME® XTRA during liquefaction in the viscometer.

Four α-amylase variants were purified and characterized for total protein and specific activity and then tested for their ability to hydrolyze/cleave corn starch in a slurry, as monitored by viscometry (HAAKE Viscotester 550 instrument). The substrate slurry was made daily as a batch with 30% corn flour dry solids. The pH was adjusted to 5.8 using sulfuric acid. The slurry 50 g (15 g dry solids) was weighed-out and pre-incubated, with stirring, for 10 minutes, to warm to 70° C. Enzymes were individually added to separate reactions unless otherwise indicated. The enzymes tested and amounts used were as follows:
Variants:
  AmySI181P variant (SEQ ID NO: 3): 44 µg,
  AmySI181A variant (SEQ ID NO: 2): 44 µg,
  AmySG182A variant (SEQ ID NO: 16): 27.5 µg,
  AmySG182S variant (SEQ ID NO: 17): 27.5 µg,
  AmySG182P variant (SEQ ID NO: 17): 27.5 µg, 687.5 µg
(results not shown).
Commercial Preparations:
  SPEZYME® XTRA (batch 1): 27.5 µg,
  SPEZYME® XTRA (batch 2): 27.5 µg, Following α-amylase addition the temperature was immediately ramped up from 70° C. to 85° C. with a stirring at 75 rpm. The temperature of the slurry and enzyme mixture was then held constant upon reaching 85° C. Viscosity was monitored throughout the incubation and for an additional 30 minutes thereafter, and reported in µNm
Results:

The results are shown in FIG. 6. The Y-axis shows the relative viscosity in µNm, and the X-axis shows time in minutes. Peak viscosity was obtained at about 10 minutes and varied with the enzyme used. The viscosity of all samples increased in the latter stages as the starch gelatinized.

Variants I181P and I181A produced greatly reduced peak viscosity compared to the commercial enzyme SPEZYME® XTRA. The I181 variants also produced a higher final viscosity than the commercial enzyme preparations. Two separate batches of SPEZYME® XTRA were used, one being freshly prepared to ensure that the differences observed were not due to any confounding factors, such as loss of activity on storage, or the like. Both batches produced similar results. Thus, the catalytic activity of the variants resulted in a lower peak viscosity, but higher final viscosity then the catalytic activity of the commercial enzymes.

The G182 variants did not perform as well as either the I181 variants or the benchmark α amylase, SPEZYME® XTRA. Both the G182A and G182P variants work for the application, although G182P variant had to be dosed at a higher amount. In one test, a dose of 687.5 µg (about 50 AAU/g) was used (results not shown).

Generally, the I181 variants performed better than the G182 variants or the SPEZYME® XTRA in terms of reducing peak viscosity, however, the SPEZYME® XTRA produced lower final viscosity than either variant type.

Example 4

Enzyme Blends Using Variants of AmyS

In addition to comparing the present α-amylase variants to commercial enzyme preparations, combinations (i.e., blends) of two commercial enzymes, or of an α-amylase variant and a commercial enzyme, were prepared and tested. Such combinations outperformed any of the other enzyme preparations, including blends of two commercial enzymes.

Figure 7A:
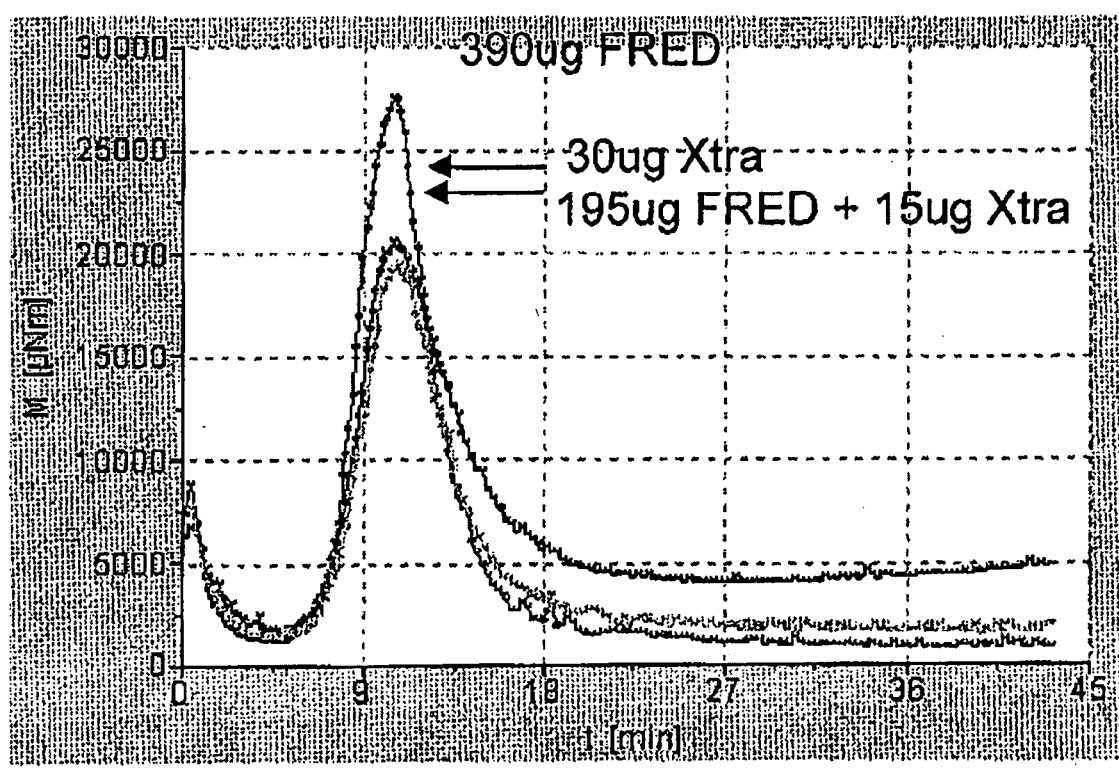
FIG. 7 shows a comparison of starch liquefaction by commercially available enzymes, variants or blends of both, using viscometry.
Figure 7B:
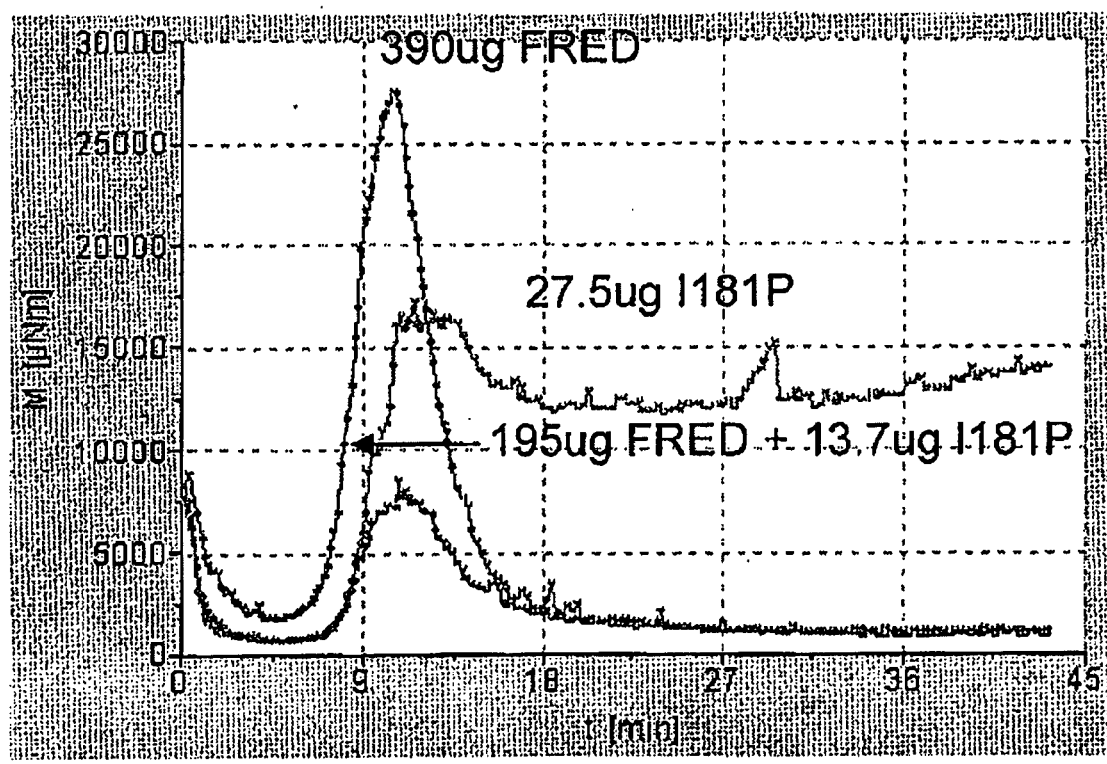

The starch slurries and enzymatic reactions for sampling were prepared and performed as detailed above in Example 3. The following enzyme activities or combinations of activities were tested:
FIG. 7A
  SPEZYME® FRED, used at 390 µg,
  SPEZYME® XTRA, used at 30 µg,
  Blend of SPEZYME® FRED and SPEZYME® XTRA, using 195 µg, and 15 µg, respectively.
FIG. 7B
  SPEZYME® FRED, used at 390 µg,
  AmyS I181P variant (SEQ ID NO: 3), used at 88 µg,
  Blend of SPEZYME® FRED and AmyS I181 variant, using at 195 µg, and 44 µg, respectively.
Results:

The results are shown in FIGS. 7A and 7B. As shown in FIG. 7A, the commercial enzyme preparations, SPEZYME® XTRA and SPEZYME® FRED (Genencor, International; described above) both produced low final viscosities, with the SPEZYME® FRED activity providing a lower final viscosity than SPEZYME® XTRA. However, the peak viscosity with SPEZYME® FRED remained considerably higher than that with SPEZYME® XTRA. In addition, SPEZYME® FRED was used at more than 10× the concentration of SPEZYME® XTRA. Interestingly, the enzyme blend containing both SPEZYME® FRED and SPEZYME® XTRA, each used at only half the concentration as when used alone, resulted in a final viscosity that was as low as that provided by SPEZYME® FRED. Moreover, the peak viscosity was reduced to that provided by the SPEZYME® XTRA activity. Therefore, the blend provides the benefit of both enzyme activities, and the disadvantages of neither; however, no synergy and little or no additive effect was evident. The peak viscosity of SPEZYME® FRED and SPEZYME® XTRA is still higher than might be desired, and substantially higher than observed with some of the α-amylase variants.

FIG. 7B shows the viscometry data for comparative slurry digests with variant I181P and SPEZYME® FRED. The peak viscosity obtained using the variant is substantially lower that for the commercial amylase preparation. However, the final viscosity is considerably higher than for either SPEZYME® FRED or SPEZYME® XTRA (not shown, see FIG. 7A). In addition, the enzyme blend containing SPEZYME® FRED and AmyS variant I181P provided the advantages of both enzymes, i.e., a lower peak viscosity than SPEZYME® FRED and a lower final viscosity than the variant amylase. Moreover, the combination blend of SPEZYME® FRED and the I181 amylase variant provided a lower peak viscosity than provided by either enzyme alone, and a final viscosity that was as low as that provided by SPEZYME® FRED. Therefore, the blend produced a lower peak viscosity combined with a lower final viscosity, showing a synergy between the two enzymes when used in combination. Thus, the present α-amylase variants are particularly useful in combination with other amylases.

It will be apparent to those skilled in the art that the α-amylase variants and the methods of making and using those amylase variants can be varied or modified without departing from the scope or spirit or of this disclosure. Thus, such variations and modifications are included within the scope of the appended claims. While the application has been divided into sections to assist the reader, a description in one section may apply to other sections. Thus headings should not be construed as limiting.

What is claimed is:

1. A variant α-amylase based on a parental α-amylase from Bacillus stearothermophilus, wherein the variant comprises a proline substitution at amino acid position 181 compared to the parental α-amylase, wherein the α-amylase variant has at least 85% sequence identity with the parent α-amylase comprising the amino acid sequence of SEQ ID NO: 1, and wherein the variant has amylase activity.

2. The variant α-amylase of claim 1, having an amino acid sequence of SEQ ID NO: 3 (I 181P).

3. The variant α-amylase of claim 1, wherein the parental α-amylase has the amino acid sequence of SEQ ID NO: 1.

4. The variant α-amylase of claim 1, having increased specific activity compared to the wild-type α-amylase, under specified assay conditions.

5. The variant α-amylase of claim 4, wherein the variant has increased specific activity between about 50-90° C.

6. The variant α-amylase of claim 5, wherein the variant has increased specific activity between about 65-85° C.

7. A composition comprising the variant α-amylase of claim 1.

8. The composition of claim 7, further comprising at least one additional enzyme.

9. The composition of claim 8, wherein the at least one additional enzyme has activity useful for liquefaction of a complex carbohydrate comprising amylose and amylopectins.

10. The composition of claim 9, wherein the at least one additional enzymes is an additional α-amylase.

11. The composition of claim 8, wherein in a liquefaction process, the composition reduces the peak viscosity of a starch slurry relative to that of a comparable starch slurry liquefied with the additional enzyme in the absence of the variant α-amylase.

12. The composition of claim 9, formulated for use in food or food processes.

13. A food-grade lyophilized composition comprising a variant α-amylase of claim 1.

14. An enzyme blend for liquefying a starch slurry, the blend comprising:
at least a first amylase according to claim 1, and a second α-amylase,
the first α-amylase having a catalytic activity that, when used in a liquefaction process, results in a final viscosity lower than, but a peak viscosity higher than, a corresponding catalytic activity of the second α-amylase, when each amylase is used alone in comparable liquefaction processes,
wherein when used in comparable liquefaction processes, the enzyme blend provides catalytic activity that results in a final viscosity about the same as that resulting from the use of the first α-amylase alone, and a peak viscosity substantially less than that resulting from the use of the second α-amylase alone;
wherein comparable liquefaction processes comprise specified conditions of temperature, pH, calcium ion concentration, and substrate concentration.

15. A kit for facilitating liquefaction of starch slurry, said kit comprising:
at least one of:
(a) a variant α-amylase according to claim 1,
(b) a composition comprising the variant α-amylase of (a),
(c) a food-grade lyophilized composition comprising the variant α-amylase of (a), or
(d) an enzyme blend comprising the variant α-amylase of (a) and a second amylase, the variant α-amylase having a catalytic activity that, when used in a liquefaction process, results in a final viscosity lower than, but a peak viscosity higher than, a corresponding catalytic activity of the second α-amylase, when each of the variant α-amylase and second amylase is used alone in comparable liquefaction processes; and
instructions for use of the kit in the liquefaction of a starch slurry.

16. The variant α-amylase of claim 1, wherein the parental α-amylase has an amino acid sequence at least 90% identical to the amino acid sequence of SEQ ID NO: 1.

17. The variant α-amylase of claim 1, wherein the parental α-amylase has an amino acid sequence at least 91% identical to the amino acid sequence of SEQ ID NO: 1.

18. The variant α-amylase of claim 1, wherein the parental α-amylase has an amino acid sequence at least 92% identical to the amino acid sequence of SEQ ID NO: 1.

19. The variant α-amylase of claim 1, wherein the parental α-amylase has an amino acid sequence at least 93% identical to the amino acid sequence of SEQ ID NO: 1.

20. The variant α-amylase of claim 1, wherein the parental α-amylase has an amino acid sequence at least 94% identical to the amino acid sequence of SEQ ID NO: 1.

21. The variant α-amylase of claim 1, wherein the parental α-amylase has an amino acid sequence at least 95% identical to the amino acid sequence of SEQ ID NO: 1.

22. The variant α-amylase of claim 1, wherein the parental α-amylase has an amino acid sequence at least 96% identical to the amino acid sequence of SEQ ID NO: 1.

23. The variant α-amylase of claim 1, wherein the parental α-amylase has an amino acid sequence at least 97% identical to the amino acid sequence of SEQ ID NO: 1.

24. The variant α-amylase of claim 1, wherein the parental α-amylase has an amino acid sequence at least 98% identical to the amino acid sequence of SEQ ID NO: 1.

25. The variant α-amylase of claim 1, wherein the parental α-amylase has an amino acid sequence at least 99% identical to the amino acid sequence of SEQ ID NO: 1.

26. A method of liquefying a starch slurry comprising:
making a slurry comprising the starch;
heating the slurry to a temperature acceptable for starch liquefaction;
adding to the slurry a composition of claim 7; and
incubating the slurry with the composition for a time and at a temperature sufficient to liquefy the starch slurry.

27. The method of claim 26, wherein the temperature is from about 50° C. to about 95° C.

28. The method of claim 27, wherein the slurry comprises about 15-40% starch on a dry-weight basis.

29. The method of claim 26, wherein the liquefaction is part of a fermentation process.

30. The method of claim 29, wherein the fermentation is used to produce a food product, a food additive, a fuel, or a fuel additive.

31. The method of claim 30, wherein the fuel or fuel additive is an alcohol.

32. The method of claim 31, wherein the alcohol is ethanol.

33. The method of claim 26, wherein the incubating step results in a peak viscosity that is reduced by at least 25% relative to the peak viscosity of a comparable slurry liquefied by the parental α-amylase.

34. A method of treating a woven material that has previously been subjected to contact with a coating comprising starch or a starch-derivative, the method comprising:
contacting the woven material with a solution comprising a variant α-amylase according to claim 1 for a time and under conditions sufficient to substantially remove the coating from the woven material.

35. The method of claim 34, wherein the woven material is a fabric.

36. The method of claim 34, wherein the contacting step is performed at a pressure that is greater then ambient atmospheric pressure.

37. A method of liquefying a starch slurry comprising making a slurry comprising the starch, heating the slurry to an acceptable temperature for liquefaction, adding the enzyme blend of claim 14 comprising said first and second α-amylases to the slurry, and incubating the slurry with the enzyme blend for a time and at a temperature sufficient to liquefy the starch slurry.

38. The method of claim 14, wherein said final viscosity is about as low as that resultant from the use of the first α-amylase alone in a comparable liquefaction process, and the peak viscosity is lower than that resultant from the use of the second α-amylase alone in a comparable liquefaction process.

39. The method of claim 14 wherein the amount of enzyme blend added results in the addition of less of each of the first and second α-amylases than the corresponding amounts of the first and second α-amylases, respectively, added when each is used alone in a comparable liquefaction process.

40. The method of claim 39, wherein the amount of each of the first and second α-amylases, respectively, is about half the corresponding amount added when each is used alone.

41. A method of producing ethanol comprising:
liquefying a starch slurry with one or more of:
(a) a variant α-amylase according to claim 1,
(b) a composition comprising the variant α-amylase of (a),
(c) a food-grade lyophilized composition comprising the variant α-amylase of (a), or
(d) an enzyme blend comprising the variant α-amylase of (a) and a second amylase, the variant α-amylase having a catalytic activity that, when used in a liquefaction process, results in a final viscosity lower than, but a peak viscosity higher than, a corresponding catalytic activity of the second α-amylase, when each of the variant α-amylase and second amylase is used alone in comparable liquefaction processes; fermenting at least a portion of the sugars in the slurry to produce ethanol; and
at least partially purifying the resultant ethanol.

42. The method of claim 41 comprising the optional step of adding one or more additional enzymes to the liquefied starch slurry to further effectuate the production of ethanol during the fermenting step.

* * * * *